(12) United States Patent
Kim et al.

(10) Patent No.: US 9,556,094 B2
(45) Date of Patent: Jan. 31, 2017

(54) MONOMER, HARDMASK COMPOSITION INCLUDING MONOMER, AND METHOD FOR FORMING PATTERN BY USING HARDMASK COMPOSITION

(71) Applicant: CHEIL INDUSTRIES INC., Gumi-si, Gyeongsangbuk-do (KR)

(72) Inventors: Yun-Jun Kim, Suwon-si (KR); Hyo-Young Kwon, Suwon-si (KR); Hea-Jung Kim, Suwon-si (KR); Chung-Heon Lee, Suwon-si (KR); Youn-Jin Cho, Suwon-si (KR); Yoo-Jeong Choi, Suwon-si (KR)

(73) Assignee: Cheil Industries, Inc., Gumi-Si, Gyeongsangbuk-do (KR)

( * ) Notice: Subject to any disclaimer, the term of this patent is extended or adjusted under 35 U.S.C. 154(b) by 0 days.

(21) Appl. No.: 14/441,241

(22) PCT Filed: Jun. 4, 2013

(86) PCT No.: PCT/KR2013/004903
§ 371 (c)(1),
(2) Date: May 7, 2015

(87) PCT Pub. No.: WO2014/104496
PCT Pub. Date: Jul. 3, 2014

(65) Prior Publication Data
US 2015/0274622 A1 Oct. 1, 2015

(30) Foreign Application Priority Data

Dec. 26, 2012 (KR) .................. 10-2012-0153750
Dec. 26, 2012 (KR) .................. 10-2012-0153751
Dec. 26, 2012 (KR) .................. 10-2012-0153752
Feb. 18, 2013 (KR) .................. 10-2013-0017054

(51) Int. Cl.
| | | |
|---|---|---|
| G03F 7/11 | (2006.01) |
| C07C 39/14 | (2006.01) |
| G03F 7/40 | (2006.01) |
| C09D 173/00 | (2006.01) |
| C07C 39/12 | (2006.01) |
| C07C 33/26 | (2006.01) |
| C07C 43/23 | (2006.01) |
| G03F 7/09 | (2006.01) |
| H01L 21/027 | (2006.01) |
| H01L 21/311 | (2006.01) |
| H01L 21/02 | (2006.01) |

(52) U.S. Cl.
CPC ............ *C07C 39/14* (2013.01); *C07C 33/26* (2013.01); *C07C 39/12* (2013.01); *C07C 43/23* (2013.01); *C09D 173/00* (2013.01); *G03F 7/09* (2013.01); *G03F 7/11* (2013.01); *G03F 7/40* (2013.01); *H01L 21/0274* (2013.01); *H01L 21/02118* (2013.01); *H01L 21/02282* (2013.01); *H01L 21/31144* (2013.01); *C07C 2103/50* (2013.01); *C07C 2103/52* (2013.01); *C07C 2103/54* (2013.01)

(58) Field of Classification Search
CPC .......... C07C 39/14; C07C 39/12; C07C 39/16; C07C 32/26; C07C 43/23; G03F 7/09; G03F 7/095; G03F 7/11; G03F 7/20; H01L 21/0274; H01L 21/02118; H01L 21/31144; H01L 21/02282
USPC ............ 430/271.1, 313, 314, 317, 322, 325, 329,430/330; 438/703; 524/553, 594; 525/534
See application file for complete search history.

(56) References Cited

U.S. PATENT DOCUMENTS

| | | | | |
|---|---|---|---|---|
| 5,663,440 A | * | 9/1997 | Sawai | ............... C07C 211/50 252/299.4 |
| 8,906,590 B2 | * | 12/2014 | Rahman | ............... C08G 61/02 430/270.1 |
| 8,952,373 B2 | * | 2/2015 | Choi | ............... H01L 21/02282 257/40 |
| 9,005,873 B2 | * | 4/2015 | Sakamoto | ............... G03F 7/091 430/270.1 |

(Continued)

FOREIGN PATENT DOCUMENTS

| CN | 101462956 A | 6/2009 |
|---|---|---|
| CN | 101462957 A | 6/2009 |

(Continued)

OTHER PUBLICATIONS

Machine translation of KR 10-2010-0080139 (no date).*

(Continued)

*Primary Examiner* — Amanda C Walke
(74) *Attorney, Agent, or Firm* — Lee & Morse, P.C.

(57) ABSTRACT

Disclosed are a monomer represented by the following Chemical Formula 1 for a hardmask composition, a hardmask composition including the monomer, and a method of forming patterns using the hardmask composition.

[Chemical Formula 1]

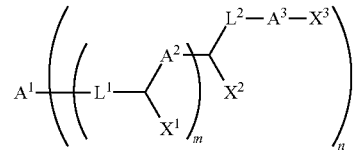

In the above Chemical Formula 1,
$A^1$ to $A^3$, $X^1$ to $X^3$, $L^1$, $L^2$, n and m are the same as described in the detailed description.

15 Claims, No Drawings

(56) References Cited

U.S. PATENT DOCUMENTS

| | | | | |
|---|---|---|---|---|
| 2005/0255651 | A1* | 11/2005 | Qian | H01L 27/11568 438/257 |
| 2011/0155944 | A1* | 6/2011 | Cho | C07C 33/26 252/62.51 R |
| 2012/0153511 | A1* | 6/2012 | Song | H01L 21/02118 257/786 |
| 2014/0186777 | A1* | 7/2014 | Lee | C07C 33/26 430/325 |
| 2015/0184018 | A1* | 7/2015 | Endo | C08G 8/02 438/703 |
| 2015/0187589 | A1* | 7/2015 | Nam | H01L 21/3081 438/703 |
| 2015/0212418 | A1* | 7/2015 | Nishimaki | C08G 8/04 438/703 |
| 2015/0301446 | A1* | 10/2015 | Shin | C07C 63/15 216/47 |
| 2015/0315333 | A1* | 11/2015 | Han | C08G 61/128 430/323 |
| 2016/0005625 | A1* | 1/2016 | Shin | H01L 21/47 438/703 |

FOREIGN PATENT DOCUMENTS

| | | |
|---|---|---|
| JP | 10-310545 A | 11/1998 |
| JP | 2008-088275 A | 4/2008 |
| JP | 2011-107684 A | 6/2011 |
| KR | 10-2002-0002910 A | 1/2002 |
| KR | 10-2004-0019332 A | 3/2004 |
| KR | 10-2007-0024512 A | 3/2007 |
| KR | 10-0833212 B1 | 5/2008 |
| KR | 10-2008-0062963 A | 7/2008 |
| KR | 10-2008-0063243 A | 7/2008 |
| KR | 10-2009-0120827 A | 11/2009 |
| KR | 10-2010-0080139 A | 7/2010 |
| KR | 10-2010-0130417 A | 12/2010 |
| KR | 10-2011-0079201 A | 7/2011 |
| KR | 10-1078709 B1 | 11/2011 |
| KR | 10-2012-0067602 A | 6/2012 |
| KR | 10-1590809 | 1/2016 |
| KR | 10-1590810 | 1/2016 |
| TW | 201226434 A | 7/2012 |
| WO | WO 03/076491 A1 | 9/2003 |

OTHER PUBLICATIONS

Search Report mailed Oct. 3, 2014 in corresponding Taiwanese Patent Application No. 102125537.

"Tritylisation of pyrene, perylene and coronene: a new family of switchable fluorescent labels", Shchepinov, et al., Tetrahedron Letters 41 (2000) 4943-4938.

Chinese Search Report dated Dec. 14, 2015 in Corresponding Chinese Patent Application No. 201380059507.8.

* cited by examiner

MONOMER, HARDMASK COMPOSITION INCLUDING MONOMER, AND METHOD FOR FORMING PATTERN BY USING HARDMASK COMPOSITION

TECHNICAL FIELD

A monomer, a hardmask composition including the monomer, and a method of forming patterns using the hardmask composition are disclosed.

BACKGROUND ART

Recently, the semiconductor industry has developed to an ultra-fine technique having a pattern of several to several tens nanometer size. Such ultrafine technique essentially needs effective lithographic techniques.

The typical lithographic technique includes providing a material layer on a semiconductor substrate; coating a photoresist layer thereon; exposing and developing the same to provide a photoresist pattern; and etching the material layer using the photoresist pattern as a mask.

Nowadays, according to small-sizing the pattern to be formed, it is difficult to provide a fine pattern having an excellent profile by only above-mentioned typical lithographic technique. Accordingly, a layer, called a hardmask layer, may be formed between the material layer and the photoresist layer to provide a fine pattern.

The hardmask layer plays a role of an intermediate layer for transferring the fine pattern of photoresist to the material layer through the selective etching process. Accordingly, the hardmask layer is required to have characteristics such as heat resistance and etch resistance, and the like to be tolerated during the multiple etching processes.

On the other hand, it has been recently suggested to form a hardmask layer by a spin-on coating method instead of the chemical vapor deposition. The spin-on coating method is easy to perform and may also improve gap-fill characteristics and planarization characteristics. The spin-on coating method may use the hardmask composition having solubility for a solvent.

However, the solubility and the characteristics required for the hardmask layer have the relationship against to each other, so a hardmask composition satisfying both is needed.

DISCLOSURE

Technical Problem

One embodiment provides a monomer for a hardmask composition that satisfies chemical resistance, heat resistance and etch resistance while ensuring solubility for a solvent, gap-fill characteristics, and planarization characteristics.

Another embodiment provides a hardmask composition including the monomer.

Yet another embodiment provides a method of forming patterns using the hardmask composition.

Technical Solution

According to one embodiment, a monomer represented by the following Chemical Formula 1 for a hardmask composition is provided.

[Chemical Formula 1]

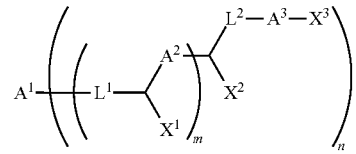

In the above Chemical Formula 1, $A^1$ to $A^3$ are each independently an aliphatic cyclic group or an aromatic cyclic group, $X^1$ to $X^3$ are each independently hydrogen, a hydroxy group, a substituted or unsubstituted amino group, a halogen atom, a halogen-containing group, or a combination thereof, $L^1$ and $L^2$ are each independently a single bond or a substituted or unsubstituted C1 to C6 alkylene group, n is an integer ranging from 1 to 5, and m is an integer ranging from 1 to 3.

The $A^1$ to $A^3$ may be each independently a substituted or unsubstituted cyclic group selected from the following Group 1.

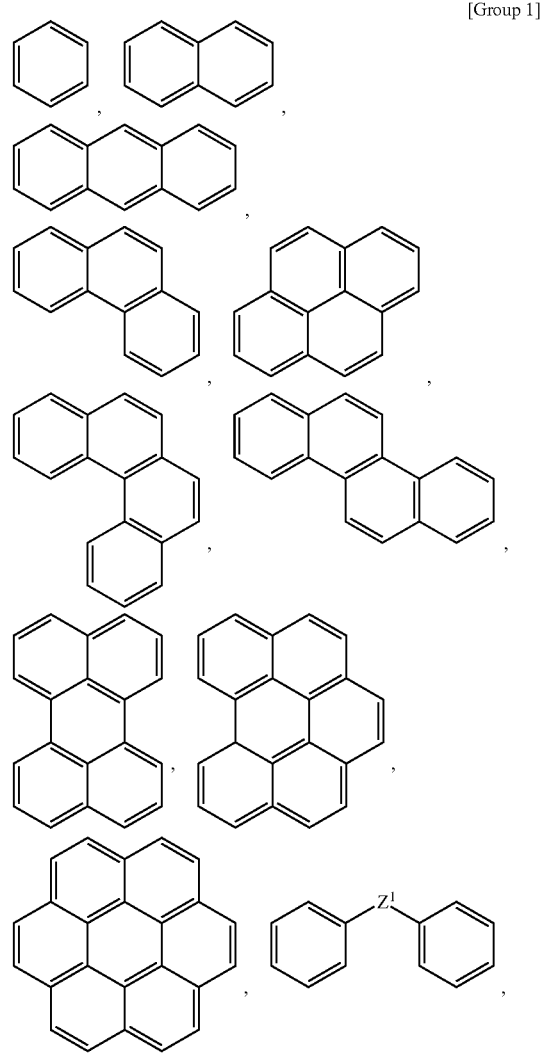

[Group 1]

-continued

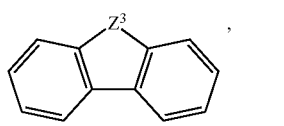
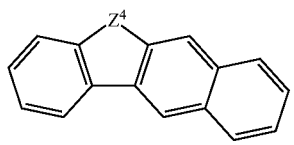
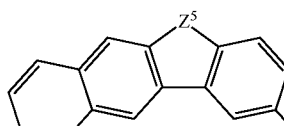
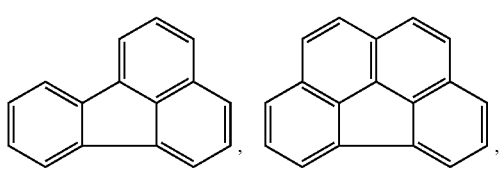
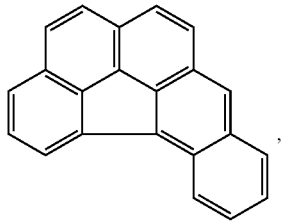
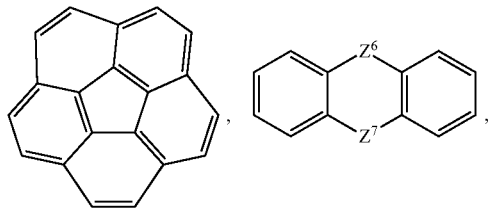
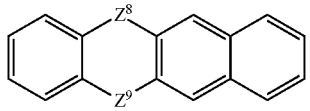
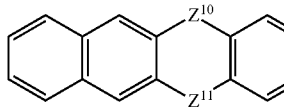
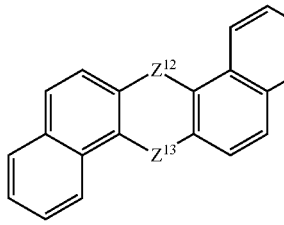
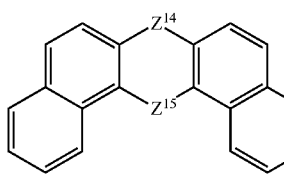

-continued

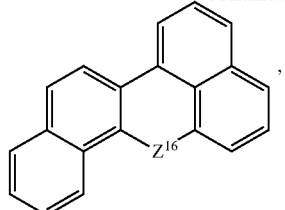
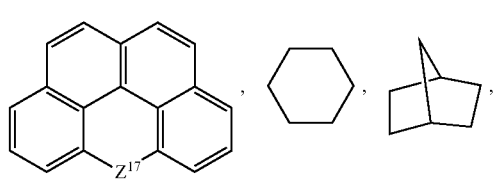
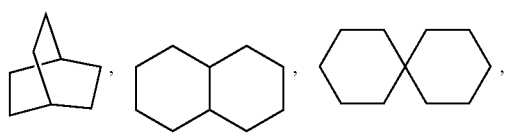
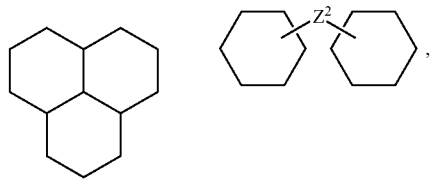
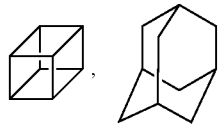

In the Group 1, $Z^1$ and $Z^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, wherein $R^a$ is hydrogen, a substituted or unsubstituted C1 to C10 alkyl group, a halogen atom, or a combination thereof, and $Z^3$ to $Z^{17}$ are independently C=O, $NR^a$, oxygen (O), sulfur (S), $CR^bR^c$, or a combination thereof, wherein $R^a$ to $R^c$ are each independently hydrogen, a substituted or unsubstituted C1 to C10 alkyl group, a halogen atom, a halogen-containing group, or a combination thereof.

At least one of the $A^1$ to $A^3$ may be a polycyclic aromatic group.

The $A^1$ and $A^3$ may be each independently a benzene group, a naphthalene group, a biphenyl group, or a pyrene group, and the $A^2$ may be a pyrene group, a perylene group, a benzoperylene group, or a coronene group.

The monomer for a hardmask composition may be represented by the following Chemical Formula 2 or 3.

[Chemical Formula 2]

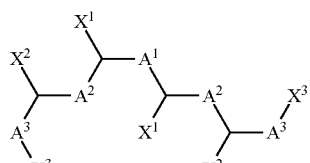

[Chemical Formula 3]

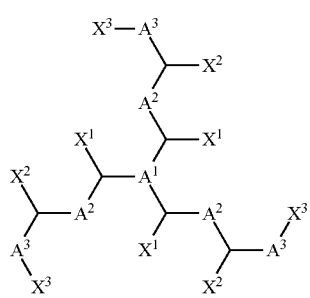

In the above Chemical Formula 2 or 3, $A^1$ to $A^3$ are each independently an aliphatic cyclic group or an aromatic cyclic group, and $X^1$ to $X^3$ are each independently hydrogen, a hydroxy group, a substituted or unsubstituted amino group, a halogen atom, a halogen-containing group, or a combination thereof.

The monomer for a hardmask composition may be represented by one selected from the following Chemical Formulae 4 to 14.

[Chemical Formula 4]

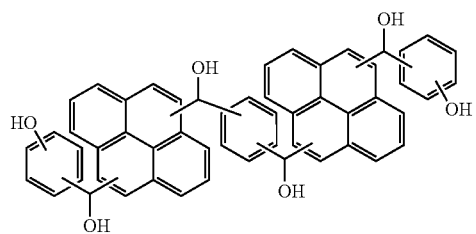

[Chemical Formula 5]

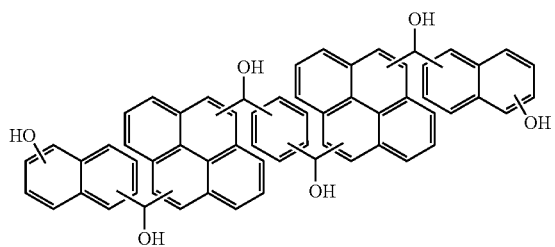

[Chemical Formula 6]

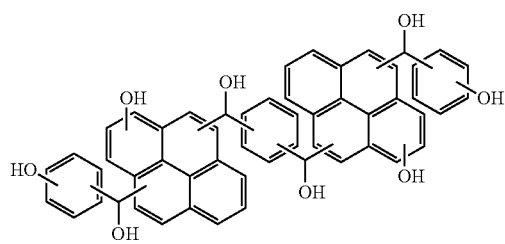

[Chemical Formula 7]

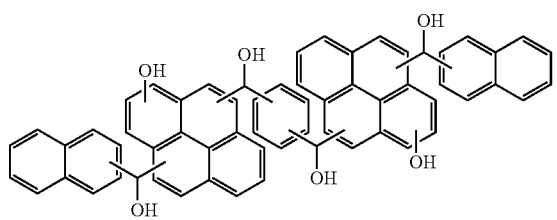

[Chemical Formula 8]

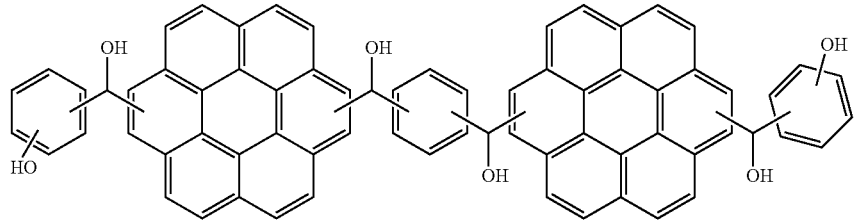

[Chemical Formula 9]

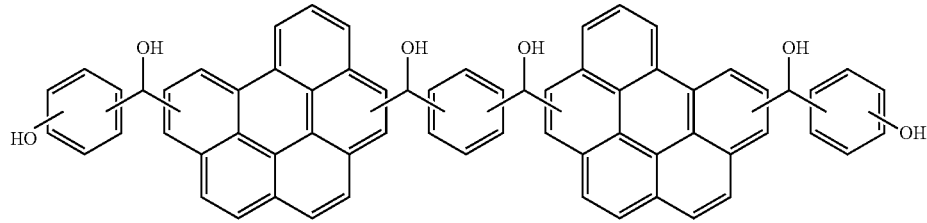

[Chemical Formula 10]
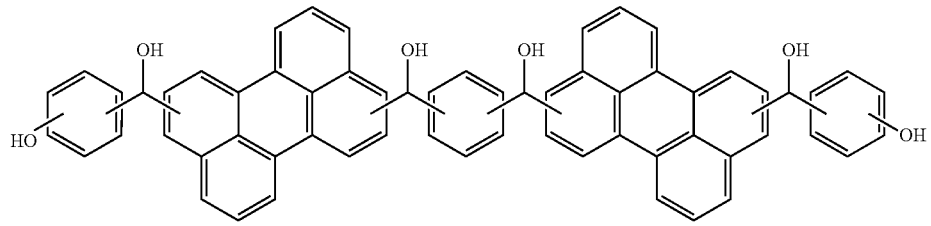
[Chemical Formula 11]
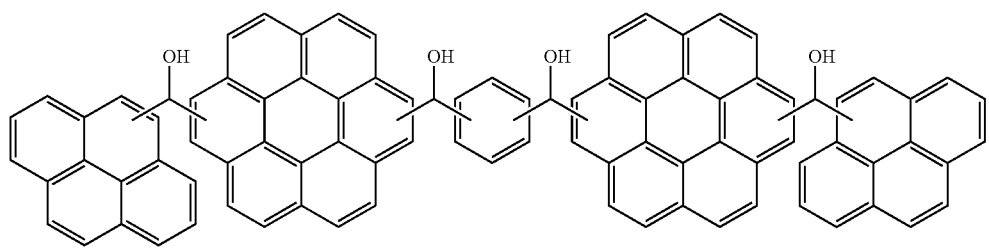
[Chemical Formula 12]
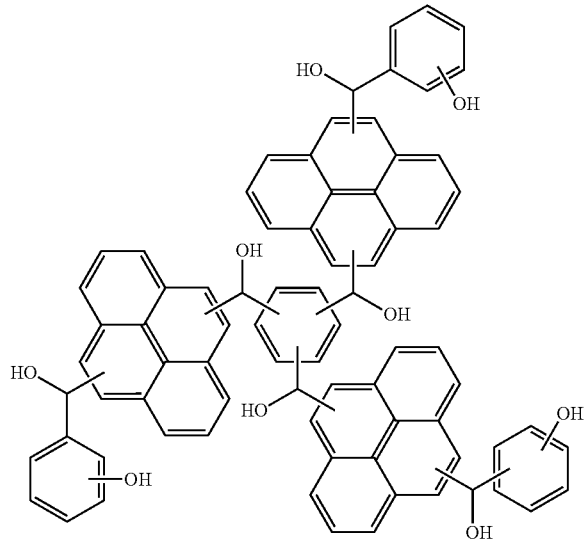
[Chemical Formula 13]
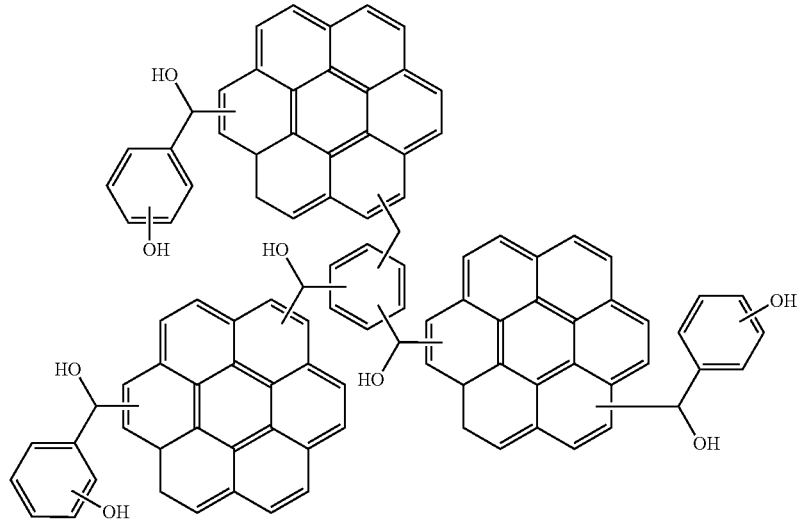

-continued

[Chemical Formula 14]

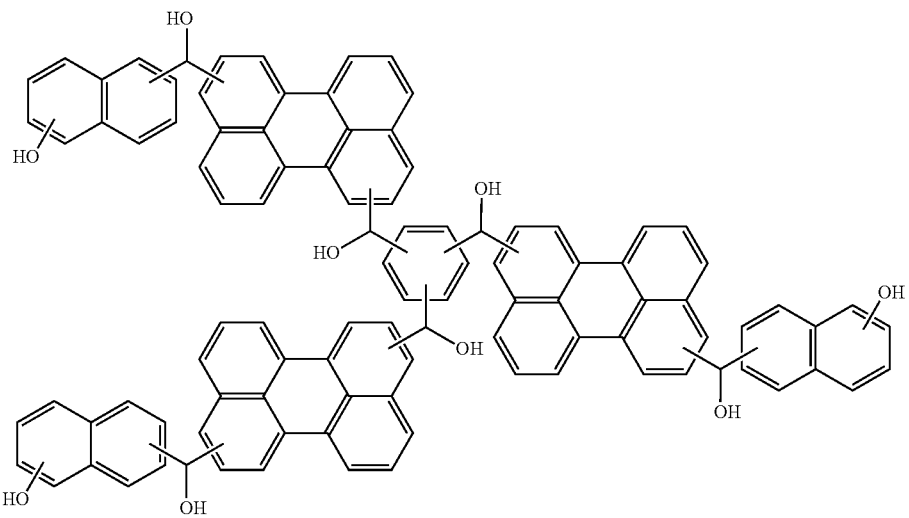

The monomer may have a molecular weight of 500 to 5,000.

According to another embodiment, a hardmask composition including a monomer represented by the following Chemical Formula 1 and a solvent is provided.

[Chemical Formula 1]

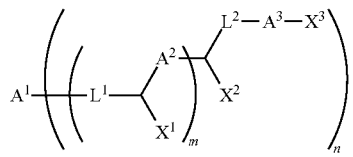

In the above Chemical Formula 1, $A^1$ to $A^3$ are each independently an aliphatic cyclic group or an aromatic cyclic group, $X^1$ to $X^3$ are each independently hydrogen, a hydroxy group, a substituted or unsubstituted amino group, a halogen atom, a halogen-containing group, or a combination thereof, $L^1$ and $L^2$ are each independently a single bond or a substituted or unsubstituted C1 to C6 alkylene group, n is an integer ranging from 1 to 5, and m is an integer ranging from 1 to 3.

The monomer may be represented by the above Chemical Formula 2 or 3.

The monomer may include at least one monomer represented by one selected from the above Chemical Formulae 4 to 14.

The monomer may have a molecular weight of 500 to 5,000.

The monomer may be included in an amount of 0.1 to 50 wt % based on the total amount of the hardmask composition.

According to another embodiment, a method of forming patterns includes providing a material layer on a substrate, applying the hardmask composition on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

Advantageous Effects

Heat resistance and etch resistance as well as solubility for a solvent, gap-fill characteristics, and planarization characteristics may be ensured.

BEST MODE

Hereinafter, exemplary embodiments of the present invention will hereinafter be described in detail so that a person skilled in the art would understand. However, this disclosure may be embodied in many different forms and is not construed as limited to the exemplary embodiments set forth herein.

In this specification, when a definition is not otherwise provided, 'substituted' refer to one substituted with a substituent selected from a halogen atom (F, Cl, Br, or I), a hydroxy group, an alkoxy group, a nitro group, a cyano group, an amino group, an azido group, an amidino group, a hydrazino group, a hydrazono group, carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of hydrogen atom of a compound.

In this specification, when a definition is not otherwise provided, 'hetero' refers to one including 1 to 3 heteroatoms selected from N, O, S, and P.

Hereinafter, a monomer for a hardmask composition according to one embodiment is described.

A monomer for a hardmask composition according to one embodiment is represented by the following Chemical Formula 1.

[Chemical Formula 1]

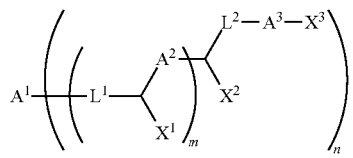

In the above Chemical Formula 1, $A^1$ to $A^3$ are cyclic groups having a substituted or unsubstituted one or two or more rings, and may be independently an aliphatic cyclic group or an aromatic cyclic group, $X^1$ to $X^3$ are each independently hydrogen, a hydroxy group, a substituted or unsubstituted amino group, a halogen atom, a halogen-containing group, or a combination thereof, $L^1$ and $L^2$ are each independently a single bond or a substituted or unsubstituted C1 to C6 alkylene group, n is an integer ranging from 1 to 5, and m is an integer ranging from 1 to 3.

The monomer includes an aliphatic cyclic group or an aromatic cyclic group having one or two or more rings in a core and substituent, and thus has rigid characteristics.

The monomer improves solubility due to a plurality of functional groups ($X^1$ to $X^3$) in each substituent, and thus may be effectively formed using a spin-on coating method, and may have improved gap-fill characteristics to fill a gap and planarization characteristics when the monomer is formed using a spin-on coating method on a lower layer having a predetermined pattern.

For example, functional groups represented by $X^1$ and $X^2$ may perform amplified cross-linkings due to a condensation reaction with a functional group represented by $X^3$, and thereby excellent cross-linking characteristics may be provided. Therefore, even though the monomer is heat-treated at a relatively low temperature, the monomer is cross-linked to form a high molecular weight polymer for a short time and thus, characteristics required in a hardmask layer such as excellent mechanical characteristics, heat resistance characteristics, chemical resistance, and etch resistance may be provided.

The $A^1$ to $A^3$ may be each independently a substituted or unsubstituted cyclic group selected from the following Group 1.

[Group 1]

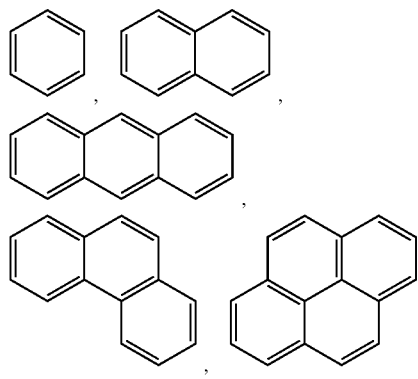

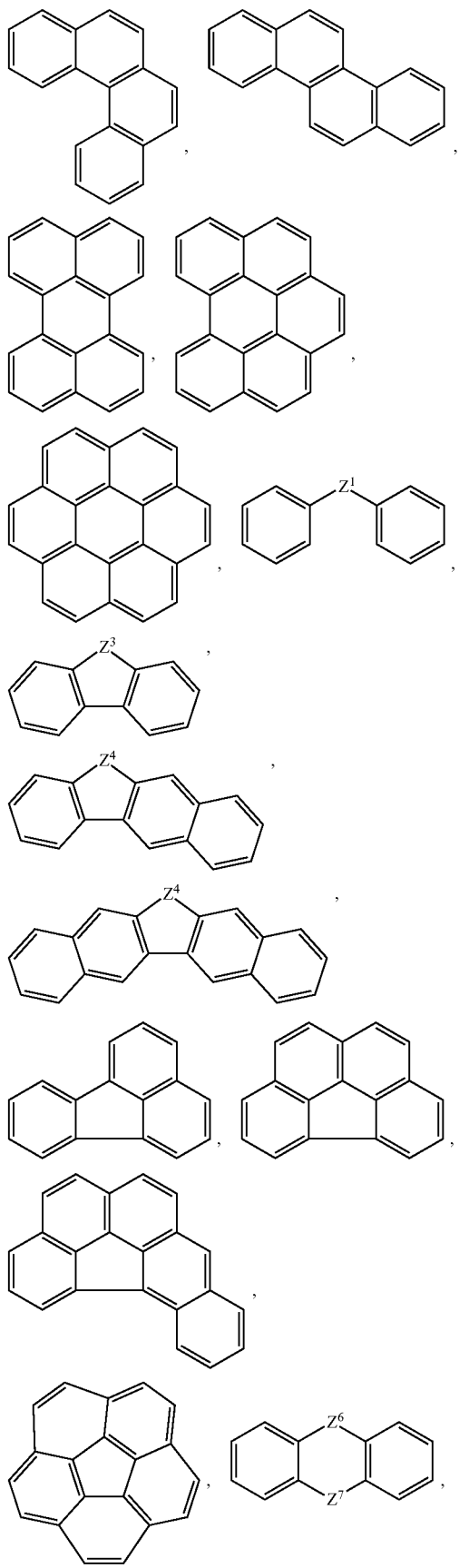

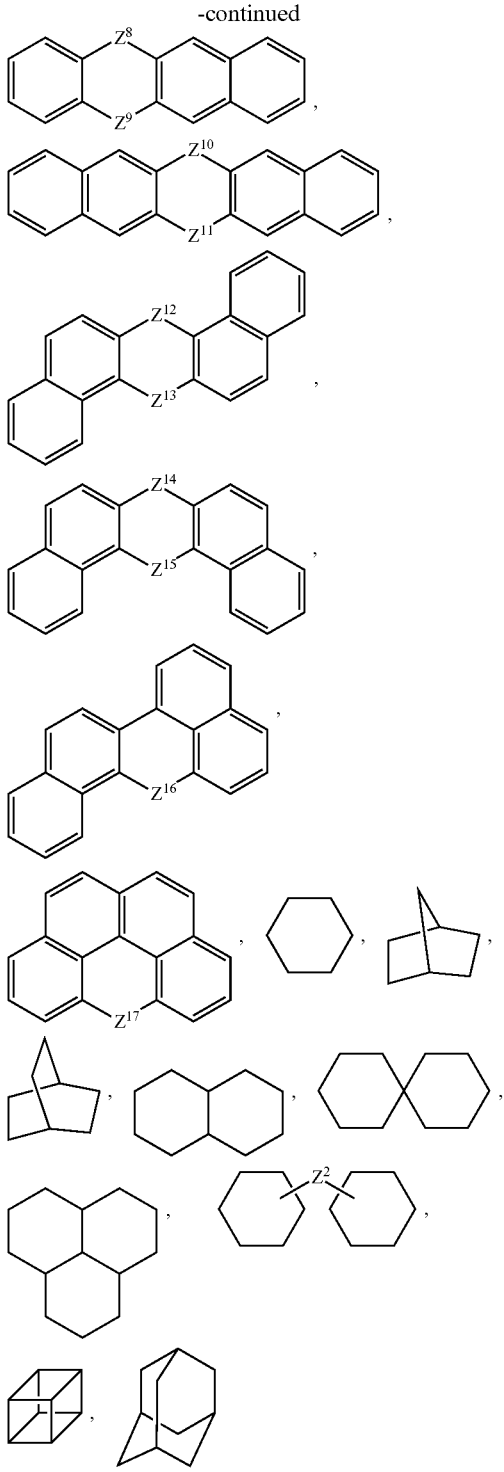

In the Group 1,

Z¹ and Z² are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein R$^a$ is hydrogen, a substituted or unsubstituted C1 to C10 alkyl group, a halogen atom, or a combination thereof, and Z³ to Z¹⁷ are independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a halogen atom, a halogen-containing group, or a combination thereof.

In the Group 1, a linking position of each ring is not particularly limited, and each ring may be substituted or unsubstituted. When the rings listed in the Group 1 is a substituted ring, it may be substituted with, for example a C1 to C20 alkyl group, a halogen atom, a hydroxy group, and the like, without limitation.

The A¹ to A³ may be, for example a substituted or unsubstituted aromatic group, for example a benzene group, a naphthalene group, a biphenyl group, a pyrene group, a perylene group, a benzoperylene group, a coronene group, or a combination thereof.

The A¹ to A³ may be, for example an aromatic group substituted with a hydroxy group, and for example may be represented by the following Chemical Formula A, when the A² is a pyrene group.

[Chemical Formula A]

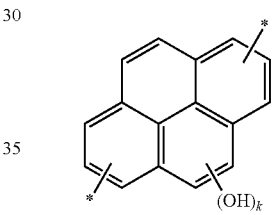

Herein, the number of a functional group is not particularly limited, and in the above Chemical Formula A, k may be an integer of 0 to 8.

At least one of the A¹ to A³ may be a polycyclic aromatic group, for example a pyrene group, a perylene group, a benzoperylene group, a coronene group, or a combination thereof.

For example, the A¹ and A³ may be each independently a benzene group, a naphthalene group, a biphenyl group, or a pyrene group, and the A² may be a pyrene group, a perylene group, a benzoperylene group, or a coronene group.

The monomer may be represented by, for example the following Chemical Formula 2 or 3.

[Chemical Formula 2]

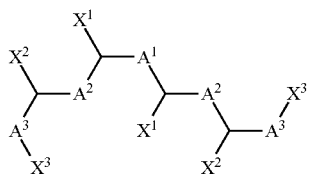

[Chemical Formula 3]

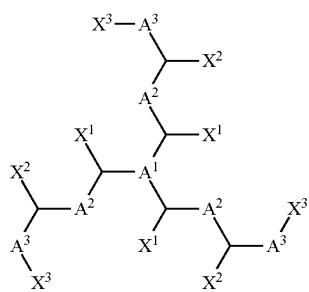

In the above Chemical Formula 2 or 3, $A^1$ to $A^3$ are each independently an aliphatic cyclic group or an aromatic cyclic group, and $X^1$ to $X^3$ are each independently hydrogen, a hydroxy group, a substituted or unsubstituted amino group, a halogen atom, a halogen-containing group, or a combination thereof.

The monomer may control properties, for example solubility by the number of a substituent. The monomer includes, for example aliphatic cyclic group or aromatic cyclic group having one or two or more rings in a core, and thus the monomer may have a compound having multiple coupling dendritic structure having three or more multiple substituents.

The monomer may be represented by, for example one selected from the following Chemical Formulae 1-1 to 1-9.

[Chemical Formula 1-1]

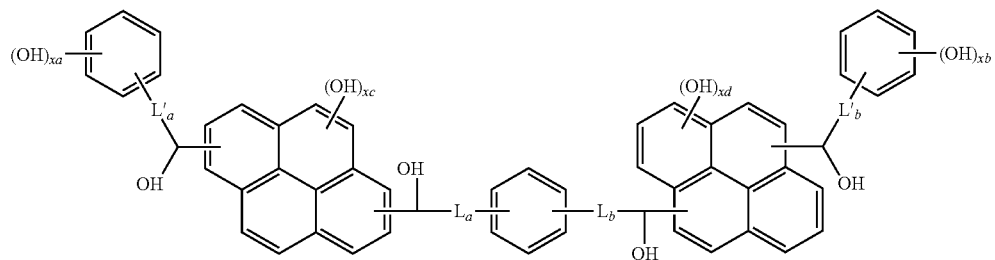

[Chemical Formula 1-2]

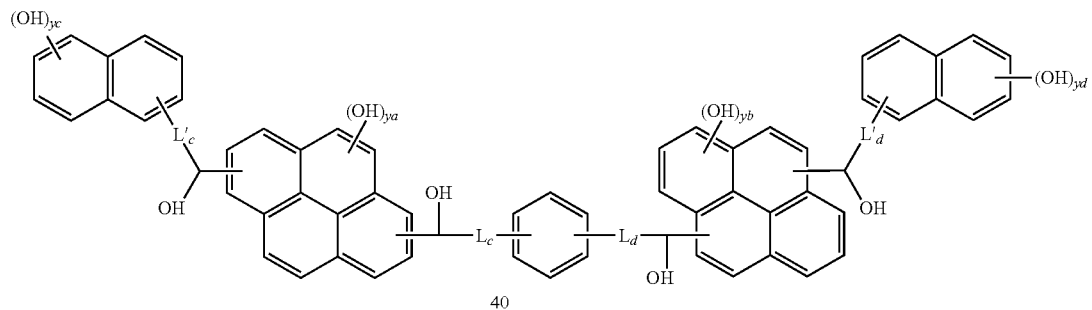

In the above Chemical Formulae 1-1 and 1-2,

La, Lb, Lc, Ld, L'a, L'b, L'c and L'd are each independently a single bond or a substituted or unsubstituted C1 to C6 alkylene group, xa and xb are each independently integers of 0 to 5, xc and xd are each independently integers of 0 to 8, ya and yb are each independently integers of 0 to 8, and yc and yd are each independently integers of 0 to 7.

[Chemical Formula 1-3]

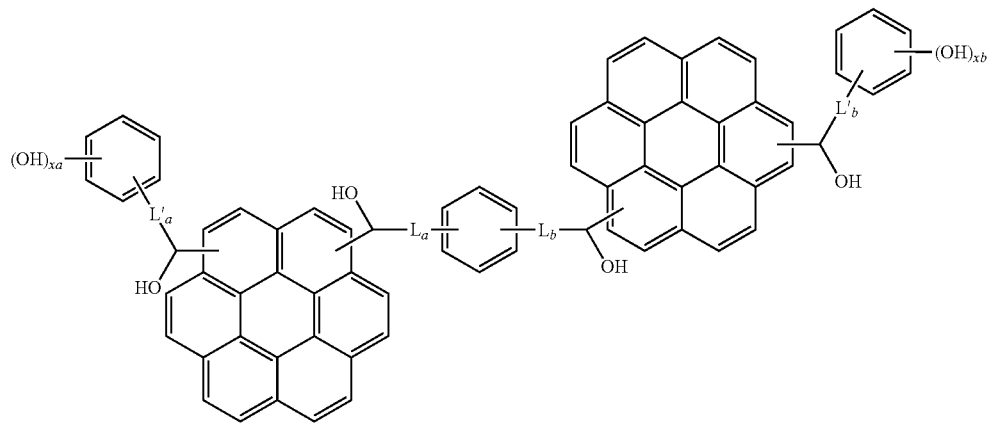

-continued
[Chemical Formula 1-4]
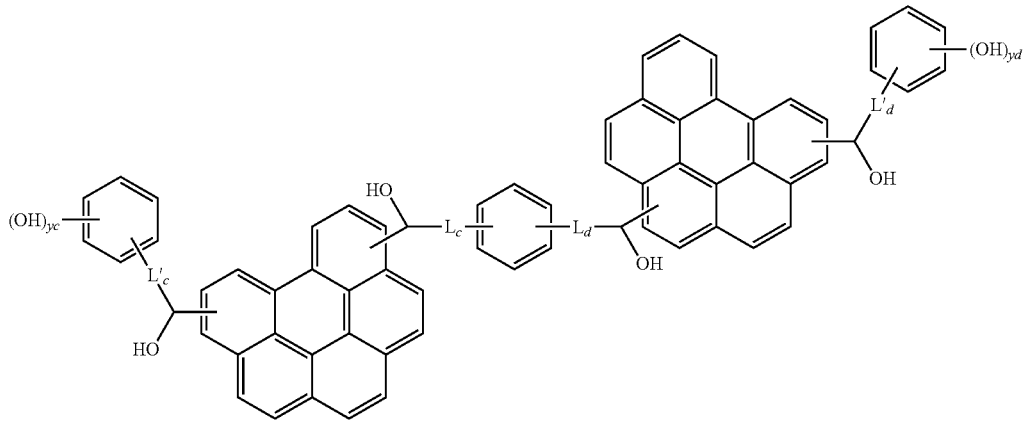
[Chemical Formula 1-5]
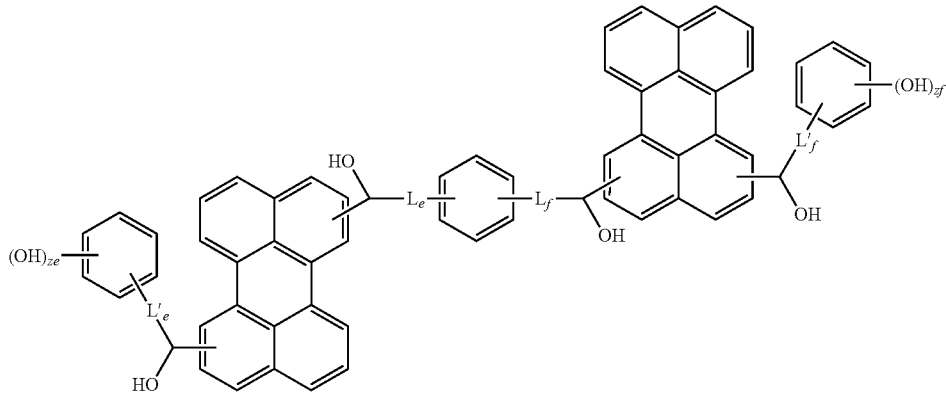
[Chemical Formula 1-6]
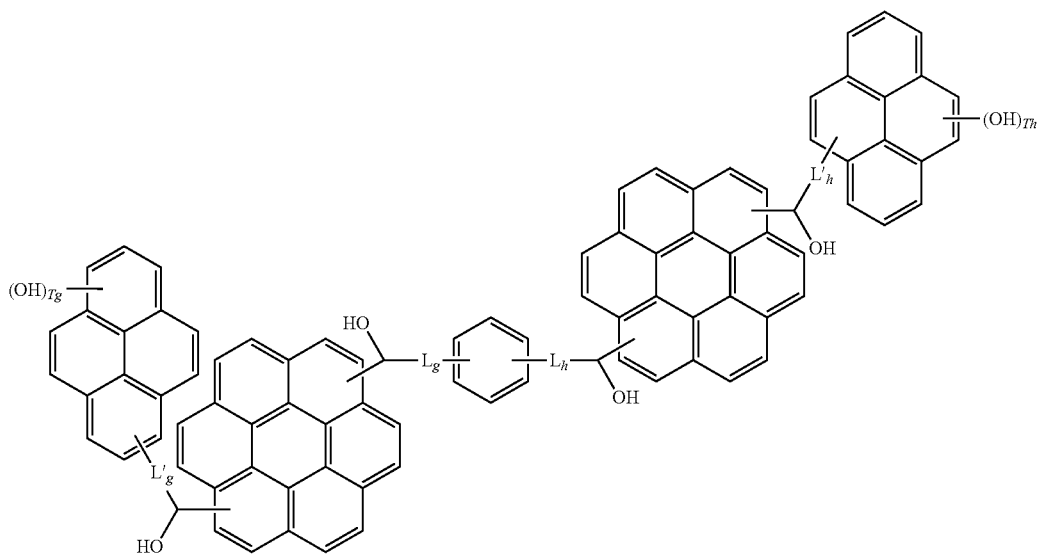
In the above Chemical Formulae 1-3, 1-4, 1-5, and 1-6, La, Lb, Lc, Ld, Le, Lf, Lg, Lh, La, L'b, L'c, L'd, L'e, L'f, L'g and L'h are each independently a single bond or a substituted or unsubstituted C1 to C6 alkylene group,
xa, xb, yc, yd, ze and zf are each independently integers of 0 to 5, and
Tg and Th are each independently integers of 0 to 9.

[Chemical Formula 1-7]
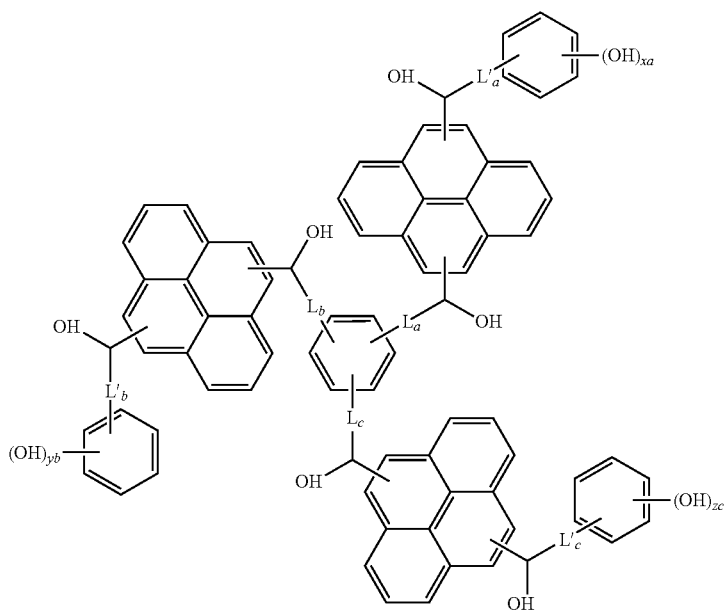
[Chemical Formula 1-8]
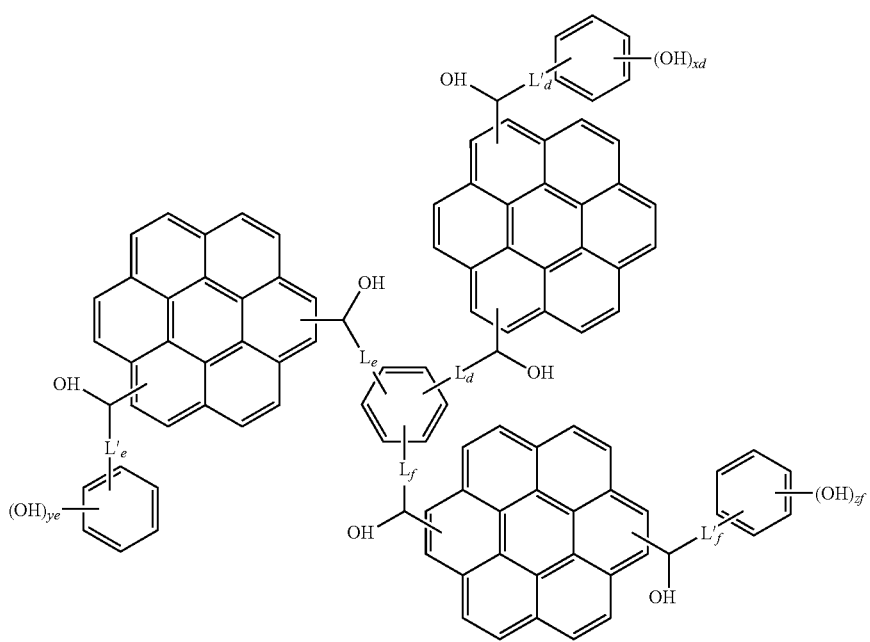

[Chemical Formula 1-9]

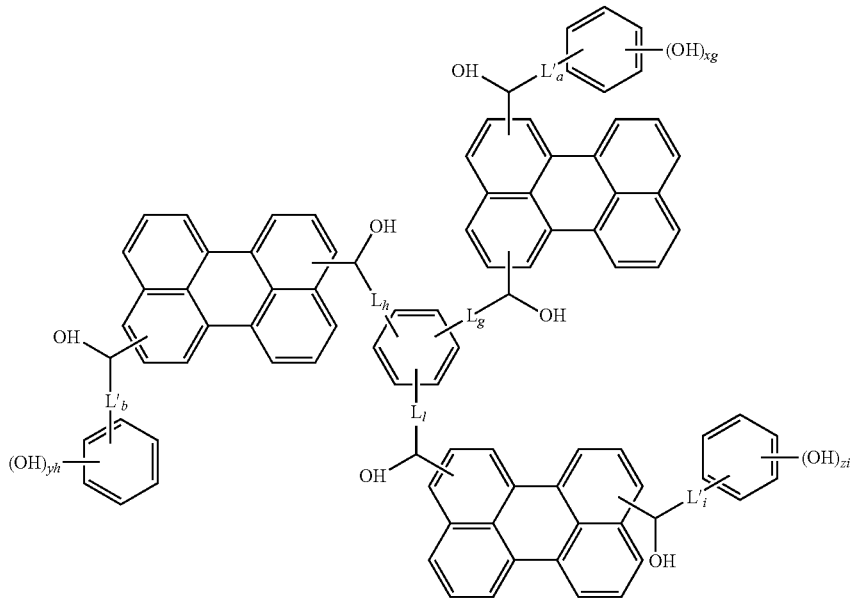

In the above Chemical Formulae 1-7, 1-8 and 1-9, La, Lb, Lc, Ld, Le, Lf, Lg, Lh, Li, L'a, L'b, L'c, L'd, L'e, L'f, L'g, L'h, and L'i are each independently a single bond or a substituted or unsubstituted C1 to C6 alkylene group, and xa, yb, zc, xd ye, zf, xg, yh, and zi are each independently integers of 0 to 5.

The monomer may be represented by for example one selected from the following Chemical Formulae 4 to 14.

[Chemical Formula 4]

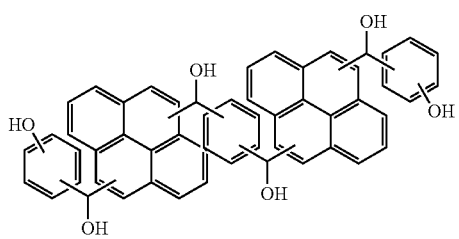

[Chemical Formula 5]

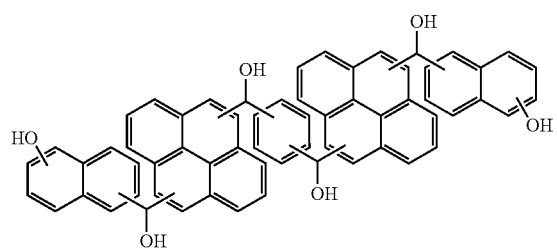

[Chemical Formula 6]

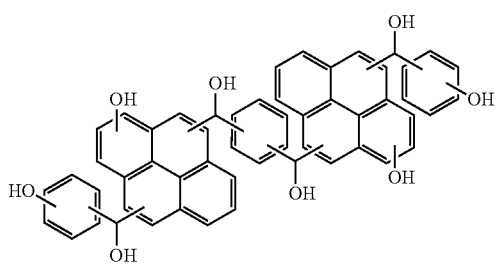

[Chemical Formula 7]

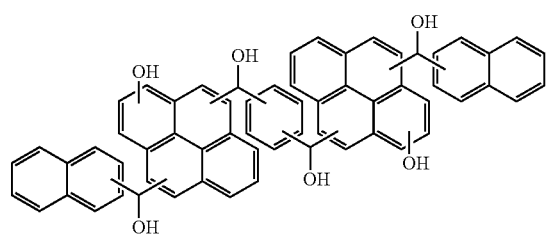

[Chemical Formula 8]

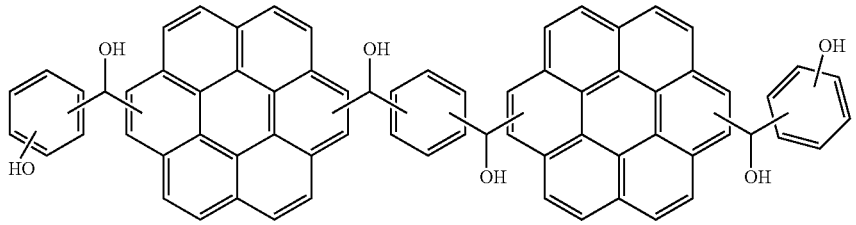

[Chemical Formula 9]
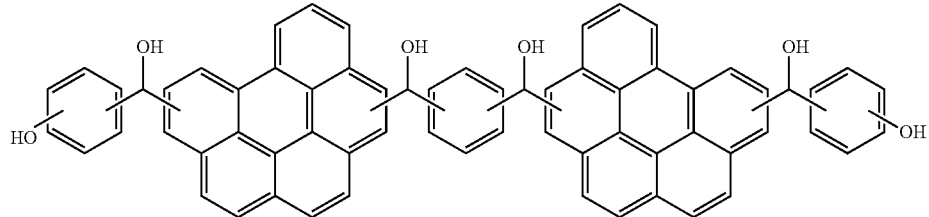
[Chemical Formula 10]
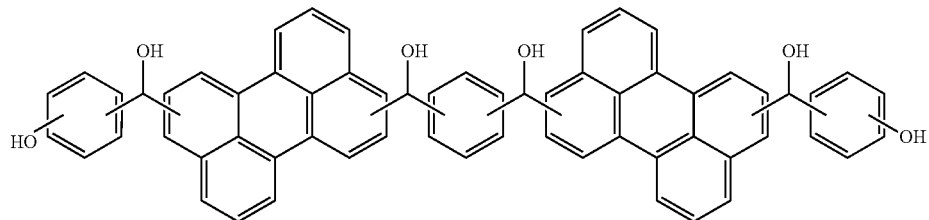
[Chemical Formula 11]
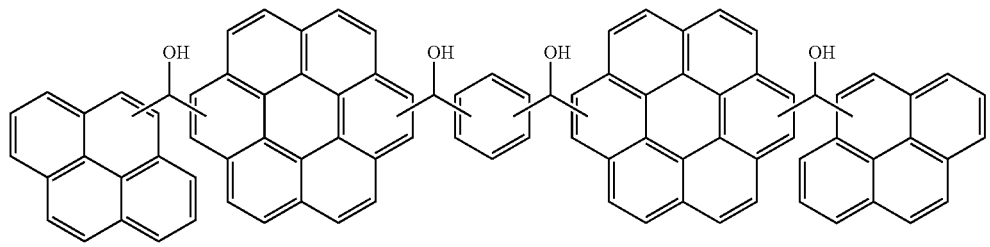
[Chemical Formula 12]
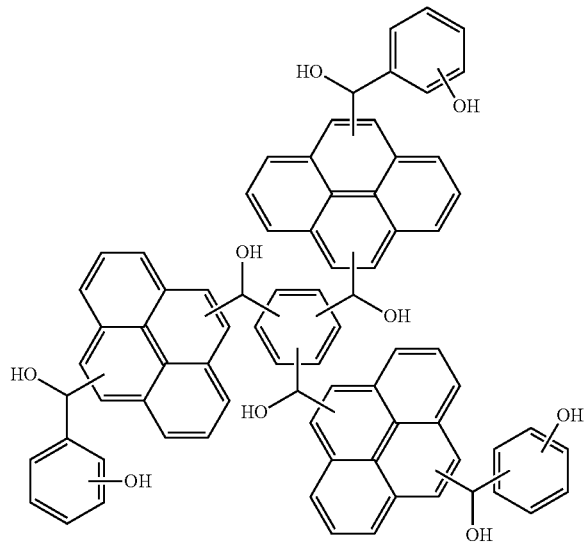

[Chemical Formula 13]

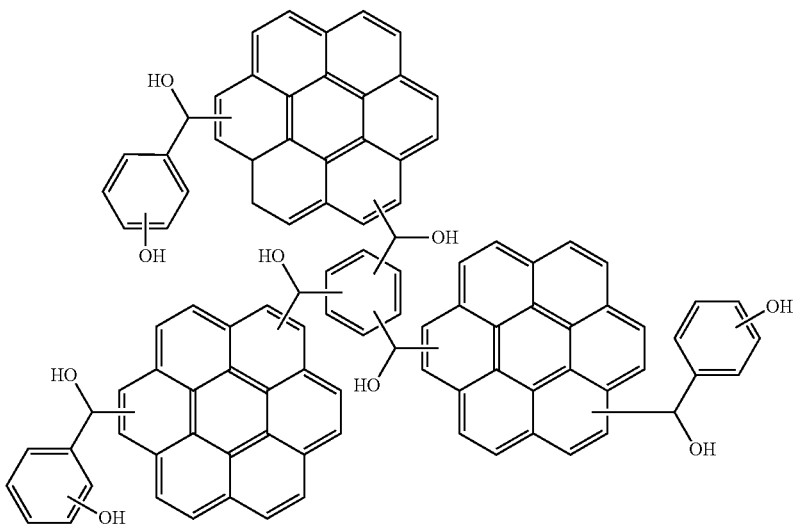

[Chemical Formula 14]

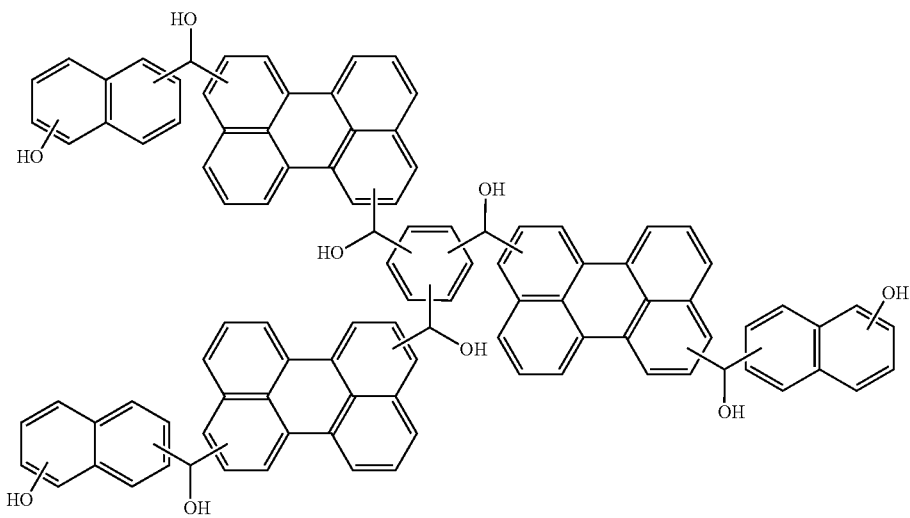

The monomer may have a molecular weight of 500 to 5,000. When the monomer has a molecular weight within the above range, solubility of the monomer having a high carbon content for a solvent is improved and an improved thin layer may be obtained through spin-on coating.

Hereinafter, a hardmask composition according to one embodiment is described.

A hardmask composition according to one embodiment includes the monomer and a solvent.

The monomer is the same as described above, and one kind of monomer may be used singularly and two or more kinds of monomers may be mixed.

The solvent may be anyone having sufficient solubility or dispersion for the monomer and may be, for example at least one selected from propylene glycol, propylene glycol diacetate, methoxy propanediol, diethylene glycol, diethylene glycol butylether, tri(ethyleneglycol)monomethylether, propylene glycol monomethylether, propylene glycol monomethylether acetate, cyclohexanone, ethyllactate, gamma-butyrolactone, methylpyrrolidone, acetylacetone, and ethyl 3-ethoxypropionate.

The monomer may be included in an amount of 1 to 50 wt % based on the total amount of the hardmask composition. When the monomer is included in the above range, a thickness of a coated thin film may be obtained.

The hardmask composition may further include a surfactant.

The surfactant may include, for example, an alkylbenzene sulfonate salt, an alkyl pyridinium salt, polyethylene glycol, or a quaternary ammonium salt, but is not limited thereto.

The surfactant may be included in an amount of 0.001 to 3 parts by weight based on 100 parts by weight of the hardmask composition. Within the amount range, the solubility may be secured while not changing the optical properties of the hardmask composition.

Hereafter, a method for forming patterns by using the hardmask composition is described.

A method of forming patterns according to one embodiment includes providing a material layer on a substrate, applying the hardmask composition including the monomer and solvent on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, for example, a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin-on coating in a form of a solution. Herein, the hardmask composition may be applied at a thickness, for example 50 Å to 50,000 Å.

The heat-treating the hardmask composition may be performed, for example 100 to 500° C. for 10 seconds to 10 minutes. During heat-treating, the monomer may cause a self cross-linking and/or mutual cross-linking reaction.

The silicon-containing thin layer may be made of, for example silicon nitride or silicon oxide.

A bottom antireflective coating (BARC) may be further formed on the silicon-containing thin layer.

Exposure of the photoresist layer may be performed using, for example ArF, KrF, or EUV. After exposure, heat treatment may be performed at 100° C. to 500° C.

The etching process of the exposed part of the material layer may be performed through a dry etching process using an etching gas and the etching gas may be, for example $CHF_3$, $CF_4$, $Cl_2$, $BCl_3$, and a mixed gas thereof.

The etched material layer may be formed in a plurality of pattern, and the plurality of pattern may be a metal pattern, a semiconductor pattern, an insulation pattern, and the like, for example diverse patterns of a semiconductor integrated circuit device.

Hereinafter, the present disclosure is illustrated in more detail with reference to examples. However, these examples are exemplary, and the present disclosure is not limited thereto.

MODE FOR INVENTION

SYNTHESIS OF MONOMER

Synthesis Example 1

21.24 g (0.105 mol) of pyrene, 17.06 g (0.1 mol) of methoxybenzoyl chloride, and 370 g of dichloromethane were put into a 1 L 3-necked flask and then, agitated with a stirring magnetic bar, and 14.67 g (0.11 mol) of trichloroaluminum was little by little added thereto at room temperature. Subsequently, the reactants were agitated at room temperature for 1 hour. When the reaction was complete, 10.15 g (0.05 mol) of terephthaloyl chloride was added to the reactants, and 29.33 g (0.22 mol) of trichloroaluminum was little by little added thereto for a reaction while being agitated. Herein, in order to control exothermic heat, reaction was performed in an ice bath for 3 hours. When the reaction was complete, the reaction products obtained as a powder was filtered using water and dried.

40 g of the dried powder, 7 g (0.125 mol) of potassium hydroxide, and 20 g (0.1 mol) of dodecane thiol, 270 g of dimethyl formamide were put into a 1 L flask, and the resultant was agitated at 100° C. for 12 hours. When the reaction was complete, the resultant was cooled down to 50° C., 37.83 g (1 mol) of sodium borohydride was little by little added thereto, and the resultant was agitated for 18 hours. When the reaction was complete, the resultant was neutralized to have pH of about 6 by using a 7% hydrogen chloride solution and extracted with ethyl acetate, obtaining a monomer represented by the following Chemical Formula 4a.

[Chemical Formula 4a]

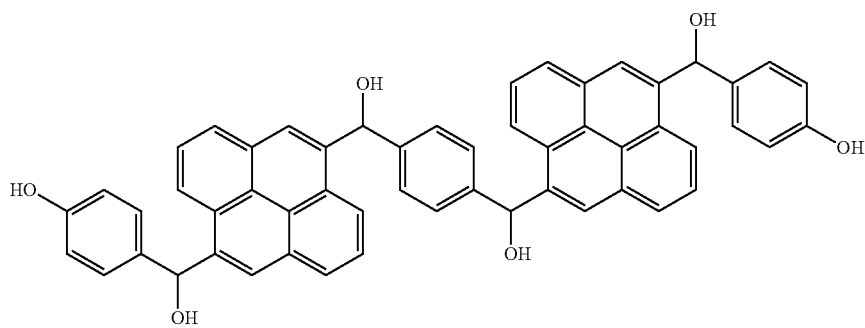

Synthesis Example 2

A monomer represented by the following Chemical Formula 5a was obtained according to the same method as Synthesis Example 1 except for to putting 22.07 g of methoxynaphthoyl chloride instead of the methoxybenzoyl chloride into a reactor.

[Chemical Formula 5a]

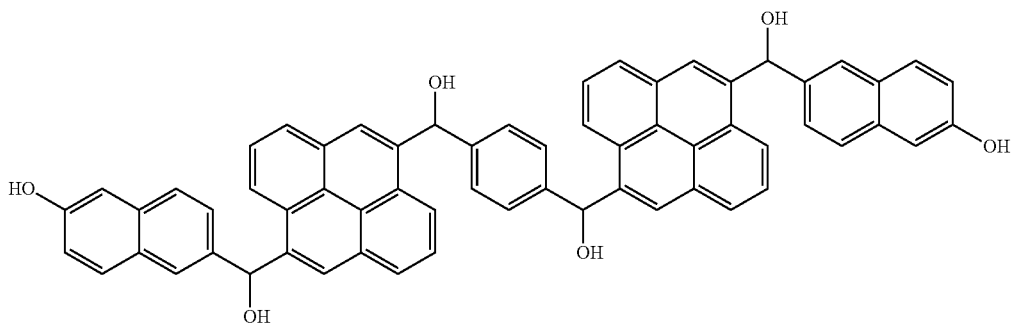

Synthesis Example 3

A monomer represented by the following Chemical Formula 6a was obtained according to the same method as Synthesis Example 1 except for putting 22.71 g of methoxy pyrene instead of the pyrene into a reactor.

[Chemical Formula 6a]

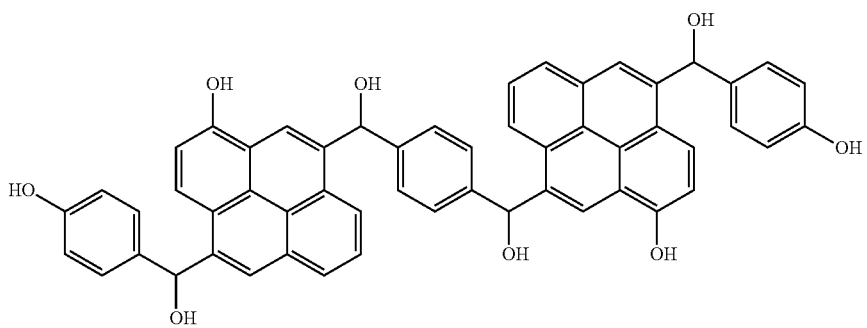

Synthesis Example 4

A monomer represented by the following Chemical Formula 7a was obtained according to the same method as Synthesis Example 1 except for putting 22.71 g of methoxypyrene instead of the pyrene and 19.06 g of naphthoyl chloride instead of the methoxybenzoylchloride into a reactor.

[Chemical Formula 7a]

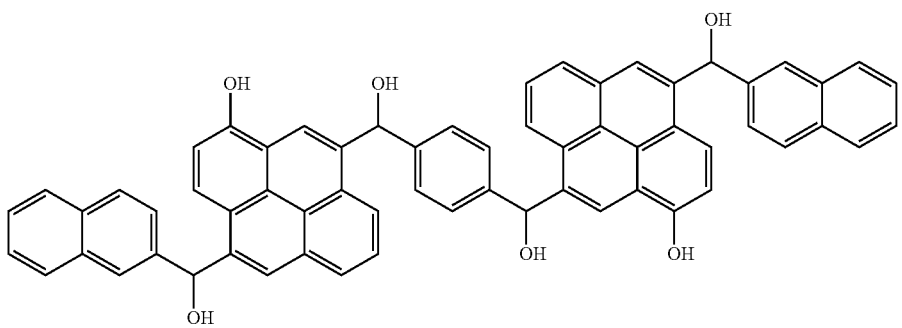

Synthesis Example 5

First Step: Friedel-Craft Acylation Reaction 40.4 g (0.1345 mol) of coronene, 22.94 g (0.1345 mol) of 4-methoxybenzoyl chloride, and 731 g of 1,2-dichloroethane were put into a flask to prepare a solution. Subsequently, aluminum chloride was slowly added to 17.9 g (0.1345 mol) of the solution, and the resultant was agitated at room temperature for 12 hours. When the reaction was complete, methanol was added thereto to obtain a precipitate, and the precipitate was filtered and dried, obtaining a compound.

10.0 g (0.02302 mol) of the compound was put into a flask along with 2.34 g (0.01151 mol) of terephthaloyl chloride and 194 g of 1,2-dichloroethane. Then, 9.21 g (0.06906 mol) of aluminum chloride was slowly added to the solution, and the resultant was agitated at room temperature for 12 hours. When the reaction was complete, methanol was added thereto to obtain a precipitate, and the precipitate was filtered and dried.

Second Step: Demethylation Reaction 10.00 g (0.01001 mol) of the compound prepared in the first step along with 10.13 g (0.05005 mol) of 1-dodecane thiol, 3.37 g (0.06006 mol) of potassium hydroxide, and 35.3 g of N,N-dimethylformamide were put into a flask and agitated at 120° C. for 8 hours. The mixture was cooled down, neutralized to have pH in a range of 6 to 7, and treated with a 5% hydrogen chloride solution to obtain a precipitate, and the precipitate was filtered and dried.

Third Step: Reduction Reaction 4.00 g (0.004120 mol) of the compound prepared in the second step along with 28.5 g of tetrahydrofuran were put into a flask. Subsequently, 3.12 g (0.08240 mol) of a sodium borohydride aqueous solution was slowly added thereto, and the resultant was agitated for 24 hours at room temperature. When the reaction was complete, the resultant was neutralized to have pH 7 by using a 5% hydrogen chloride solution and precipitated by using ethyl acetate, and the precipitate was dried and dried, obtaining a compound represented by the following Chemical Formula 8a.

[Chemical Formula 8a]

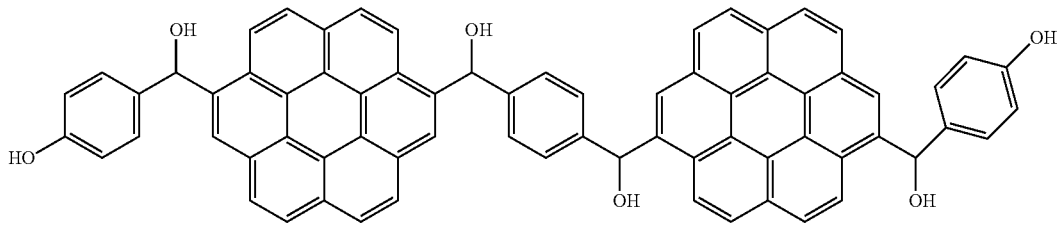

Synthesis Example 6

A compound represented by the following Chemical Formula 8b was prepared according to the same method as Synthesis Example 1 except for using 2.34 g (0.01151 mol) of isophthaloyl chloride instead of the terephthaloyl chloride in the first step.

[Chemical Formula 8b]

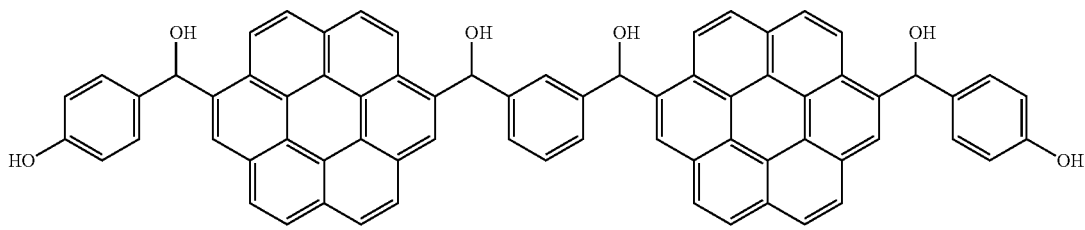

Synthesis Example 7

First Step: Friedel-Craft Acylation Reaction 20.0 g (0.07239 mol) of benzoperylene, 12.4 g (0.07239 mol) of 4-methoxybenzoylchloride, and 378 g of 1,2-dichloroethane were put into a flask to prepare a solution. Subsequently, 9.65 g (0.07239 mol) of aluminum chloride was slowly added to the solution, and the resultant was agitated at room temperature for 12 hours. When the reaction was complete, methanol was added thereto for precipitation, and a precipitate obtained therefrom was filtered and dried, obtaining a compound.

9.77 g (0.02380 mol) of the compound prepared in the first step, 2.42 g (0.01190 mol) of isophthaloyl chloride, and 195 g of 1,2-dichloroethane were put into a flask. Then, 9.52 g (0.07140 mol) of aluminum chloride was slowly added to the solution, and the resultant was agitated at room temperature for 12 hours. When the reaction was complete, methanol was added thereto, and a precipitate prepared therefrom was filtered and dried.

Second Step: Demethylation Reaction 5.94 g (0.006250 mol) of the compound prepared in the first step, 6.33 g (0.03125 mol) of 1-dodecanethiol, 2.10 g (0.03750 mol) of potassium hydroxide, and 21.6 g of N,N-dimethyl formamide were put into a flask, and the resultant was agitated at 120° C. for 8 hours. The mixture was cooled and neutralized to have pH 6 to 7 by using a 5% hydrogen chloride solution, and a precipitate obtained therefrom was filtered and dried.

Third Step: Reduction Reaction 2.85 g (0.003090 mol) of the compound obtained in the second step and 20.8 g of tetrahydrofuran were put into a flask. 2.34 g (0.06180 mol) of a sodium borohydride aqueous solution was slowly added to the solution, and the resultant was agitated for 24 hours at room temperature. When the reaction was complete, the resultant was neutralized to have pH 7 by using a 5% hydrogen chloride solution and extracted by using ethyl acetate, and a precipitate obtained therefrom was dried, obtaining a compound represented by the following Chemical Formula 9a.

Synthesis Example 8

First Step: Friedel-Craft Acylation Reaction 18.5 g (0.07330 mol) of perylene, 12.5 g (0.07330 mol) of 4-methoxybenzoylchloride, and 367 g of 1,2-dichloroethane were put into a flask to prepare a solution. 9.77 g (0.07330 mol) of aluminum chloride was slowly added to the solution, and the resultant was agitated at room temperature for 12 hours. When the reaction was complete, methanol was added thereto, and a precipitate obtained therefrom and filtered and dried, obtaining a compound.

Subsequently, 7.00 g (0.01812 mol) of the compound, 1.84 g (0.009060 mol) of isophthaloyl chloride, and 145 g of 1,2-dichloroethane were put into a flask. 7.25 g (0.05436 mol) of aluminum chloride was slowly added to the solution, and the resultant was agitated at room temperature for 12 hours. When the reaction was complete, methanol was added thereto, and a precipitate obtained therefrom was filtered and dried.

Second Step: Demethylation Reaction 7.00 g (0.007750 mol) of the compound obtained in the first step, 7.84 g (0.03875 mol) of 1-dodecane thiol, 2.61 g (0.04650 mol) of potassium hydroxide, and 26.2 g of N,N-dimethyl formamide were put into a flask, and the resultant was agitated at 120° C. for 8 hours. The mixture was cooled down and neutralized with a 5% hydrogen chloride solution to have pH 6 to 7, and a precipitate obtained therefrom was filtered and dried.

Third Step: Reduction Reaction 5.00 g (0.005720 mol) of the compound prepared in the second step was put into a flask, and 37.3 g of tetrahydrofuran was added thereto. 4.33 g (0.1144 mol) of a sodium borohydride aqueous solution was slowly added to the solution, and the resultant was agitated at room temperature for 24 hours. When the reaction was complete, the resultant was neutralized into have about pH 7 by using a 5% hydrogen chloride solution and extracted by using ethyl acetate, and the resultant was dried, obtaining a compound represented by the following Chemical Formula 10a.

[Chemical Formula 9a]

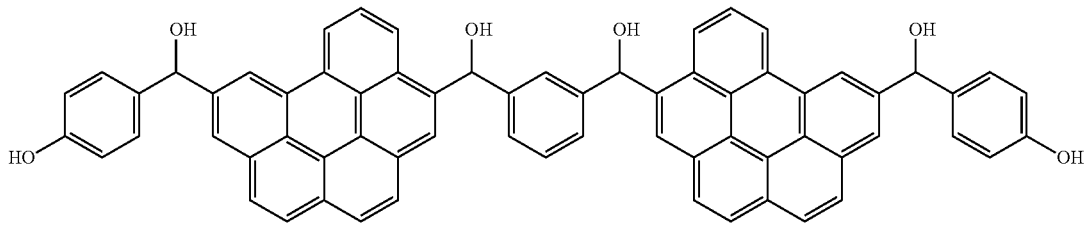

[Chemical Formula 10a]

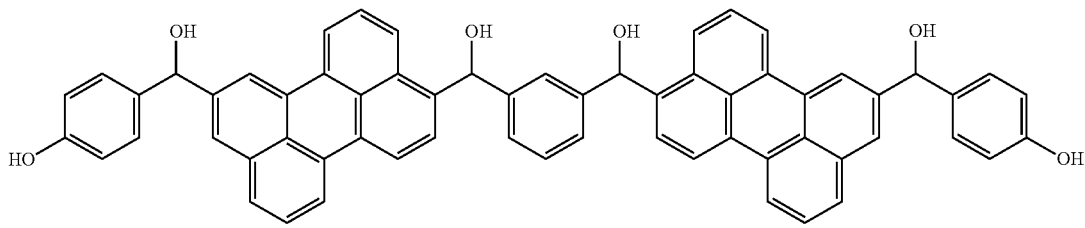

Synthesis Example 9

First Step: Friedel-Craft Acylation Reaction 10.0 g (0.03329 mol) of coronene, 8.81 g (0.03329 mol) of 1-pyrenecarbonylchloride, and 209 g of 1,2-dichloroethane were put into a flask to prepare a solution. Subsequently, 4.44 g (0.03329 mol) of aluminum chloride was slowly added to the solution, and the resultant was agitated at room temperature for 12 hours. When the reaction was complete, methanol was added thereto, and a precipitate was filtered and dried, obtaining a compound.

Subsequently, 10.0 g (0.01892 mol) of the compound, 1.92 g (0.00946 mol) of isophthaloyl chloride, and 175 g of 1,2-dichloroethane were put into a flask. 7.57 g (0.05675 mol) of aluminum chloride was slowly added thereto, and the resultant was agitated at room temperature for 12 hours. When the reaction was complete, methanol was added thereto, and a precipitate obtained therefrom was filtered and dried.

Second Step: Reduction Reaction 5.00 g (0.004211 mol) of the compound prepared in the first step and 32.7 g of tetrahydrofuran were put into a flask. 3.19 g (0.08423 mol) of a sodium borohydride aqueous solution was slowly added to the solution, and the resultant was agitated for 24 hours at room temperature. When the reaction was complete, the resultant was neutralized to have about pH 7 by using a 5% hydrogen chloride solution and extracted by using ethyl acetate, and the resultant was dried, obtaining a compound represented by the following Chemical Formula 11a.

ane were put into a flask to prepare a solution. Subsequently, 6.59 g (0.0494 mol) of aluminum chloride was slowly added to the solution, and the resultant was agitated at room temperature for 2 hours. When the reaction was complete, a precipitate obtained by adding methanol to the solution was filtered and dried, obtaining a compound.

15.46 g (0.0460 mol) of the compound, 4.07 g (0.0153 mol) of 1,3,5-benzene tricarboxylic acid chloride, and 102.62 g of 1,2-dichloroethane were put into a flask to prepare a solution. Subsequently, 6.13 g (0.0460 mol) of aluminum chloride was slowly added to the solution, and the resultant was agitated at room temperature for 6 hours. When the reaction was complete, methanol was added to the solution, and a precipitate obtained therefrom was filtered and dried.

Second Step: Demethylation Reaction 15.17 g (0.0130 mol) of the compound, 13.18 g (0.0651 mol) of 1-dodecane thiol, 4.38 g (0.0781 mol) of potassium hydroxide, and 76.37 g of N,N-dimethylformamide were put into a flask and agitated at 120° C. for 3 hours. Subsequently, the mixture was cooled down and neutralized to have about pH 6-7 by using a 5% hydrogen chloride solution, and a precipitate obtained therefrom was filtered and dried.

Third Step: Reduction Reaction 11.84 g (0.0105 mol) of the compound and 40 g of tetrahydrofuran were put into a flask to prepare a solution. Subsequently, 7.98 g (0.2108 mol) of a sodium borohydride aqueous solution was slowly added to the solution, and the resultant was agitated at room temperature for 24 hours.

[Chemical Formula 11a]

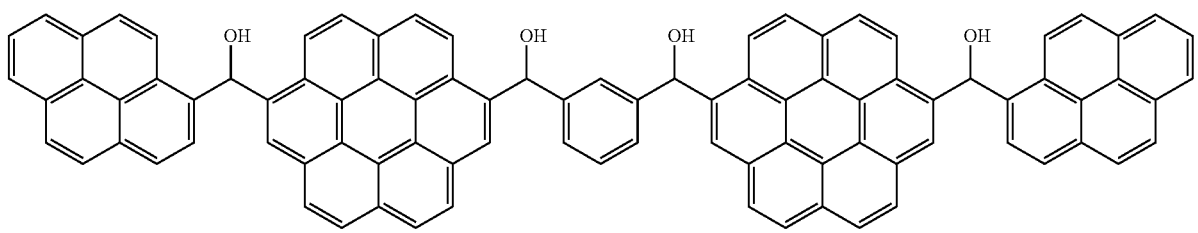

Synthesis Example 10

First Step: Friedel-Craft Acylation Reaction 10 g (0.0494 mol) of pyrene, 8.43 g (0.0494 mol) of 4-methoxybenzoylchloride, and 100.11 g of 1,2-dichloroeth- When the reaction was complete, the resultant was neutralized into pH 7 by using a 5% hydrogen chloride solution and extracted by using ethyl acetate, and the resultant was dried, obtaining a compound represented by the following Chemical Formula 12a.

[Chemical Formula 12a]

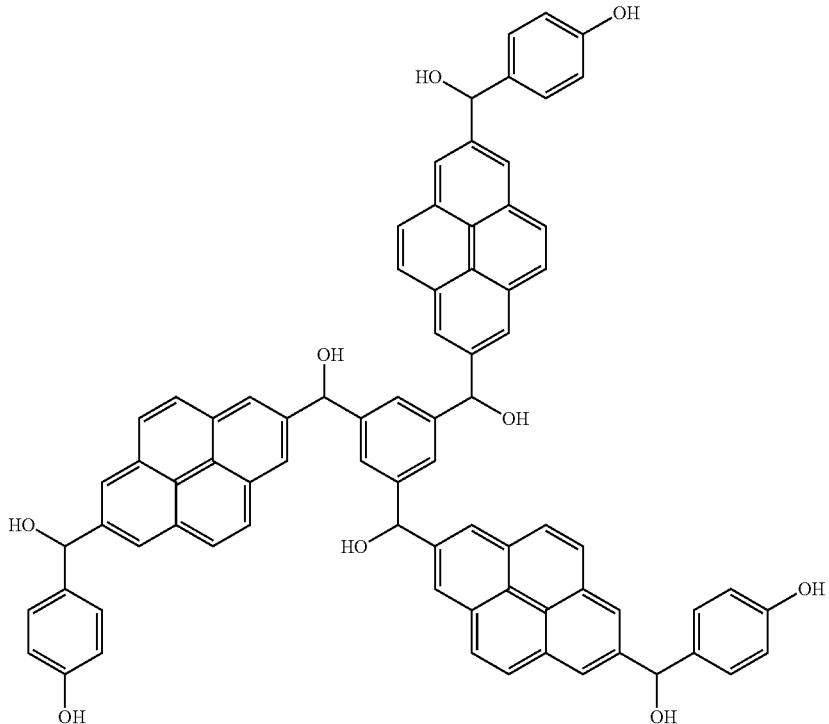

Synthesis Example 11

First Step: Friedel-Craft Acylation Reaction 10 g (0.0333 mol) of coronene, 5.68 g (0.0333 mol) of 4-methoxybenzoyl chloride, and 80.48 g of 1,2-dichloroethane were put into a flask to prepare a solution. 4.44 g (0.0333 mol) of aluminum chloride was slowly added to the solution, and the resultant was agitated at room temperature for 4 hours. When the reaction was complete, methanol was added thereto, and a precipitate obtained therefrom was filtered and dried.

12.00 g (0.0276 mol) of the compound, 2.44 g (0.0092 mol) of 1,3,5-benzenetricarboxylic acid chloride, and 72.51 g of 1,2-dichloroethane were put into a flask to prepare a solution. 3.68 g (0.0276 mol) of aluminum chloride was slowly added to the solution, and the resultant was agitated at room temperature for 12 hours. When the reaction was complete, methanol was added thereto, and a precipitate obtained therefrom was filtered and dried.

Second Step: Demethylation Reaction 10.61 g (0.0073 mol) of the compound, 7.36 g (0.0363 mol) of 1-dodecane thiol, 2.45 g (0.0436 mol) of potassium hydroxide, and 47.63 g of N,N-dimethyl formamide were put into a flask and agitated at 120° C. for 5 hours. Subsequently, the mixture was cooled down and neutralized to have about pH 6-7 by using a 5% hydrogen chloride solution, and a precipitate obtained therefrom was filtered and dried.

Third Step: Reduction Reaction 9.84 g (0.0067 mol) of the compound and 30 g of tetrahydrofuran were put into a flask to prepare a solution. 5.06 g (0.1337 mol) of a sodium borohydride aqueous solution was slowly added to the solution, and the resultant was agitated at room temperature for 24 hours. When the reaction was complete, the resultant was neutralized to have about pH 7 by using a 5% hydrogen chloride solution and extracted by using ethyl acetate, and the resultant was dried, obtaining a compound represented by the following Chemical Formula 13a.

[Chemical Formula 13a]

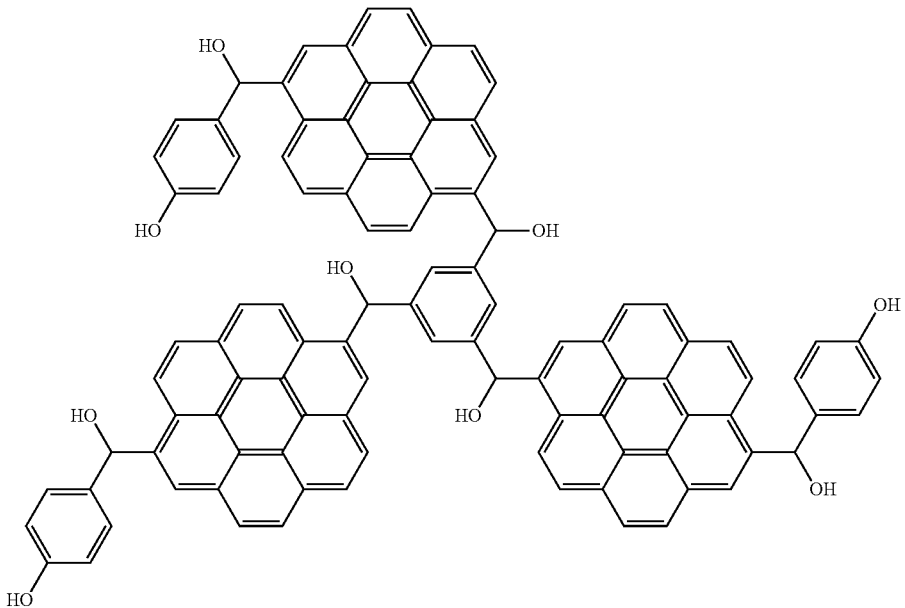

Synthesis Example 12

First Step: Friedel-Craft Acylation Reaction 15 g (0.0595 mol) of perylene, 13.12 g (0.0595 mol) of 6-methoxynaphthalene-2-carbonyl chloride, and 144.18 g of 1,2-dichloroethane were put into a flask to prepare a solution. Subsequently, 7.93 g (0.0595 mol) of aluminum chloride was slowly added to the solution, and the resultant was agitated at room temperature for 5 hours. When the reaction was complete, methanol was added thereto, and a precipitate obtained therefrom was filtered and dried.

22.80 g (0.0522 mol) of the compound, 4.62 g (0.0174 mol) of 1,3,5-benzene tricarboxylic acid chloride, and 137.55 g of 1,2-dichloroethane were put into a flask to prepare a solution. Subsequently, 6.96 g (0.0522 mol) of aluminum chloride was slowly added to the solution, and the resultant was agitated at room temperature for 12 hours. When the reaction was complete, methanol was added thereto, and a precipitate obtained therefrom was filtered and dried.

Second Step: Demethylation Reaction 15.00 g (0.0102 mol) of the compound, 12.43 g (0.0819 mol) of 1-dodecanethiol, 4.59 g (0.0819 mol) of potassium hydroxide, and 74.72 g of N,N-dimethylformamide were put into a flask and agitated at 120° C. for 12 hours. Subsequently, the mixture was cooled down and neutralized to have about pH 6-7 by using a 5% hydrogen chloride solution, and a precipitate obtained therefrom was filtered and dried.

Third Step: Reduction Reaction 10.50 g (0.0074 mol) of the compound and 22 g of tetrahydrofuran were put into a flask to prepare a solution. 8.37 g (0.2213 mol) of a sodium borohydride aqueous solution was slowly added to the solution, and the resultant was agitated at 50° C. for 24 hours. When the reaction was complete, the resultant was neutralized to have about pH 7 by using a 5% hydrogen chloride solution and extracted by using ethyl acetate, and the resultant was dried, obtaining a compound represented by the following Chemical Formula 14a.

[Chemical Formula 14a]

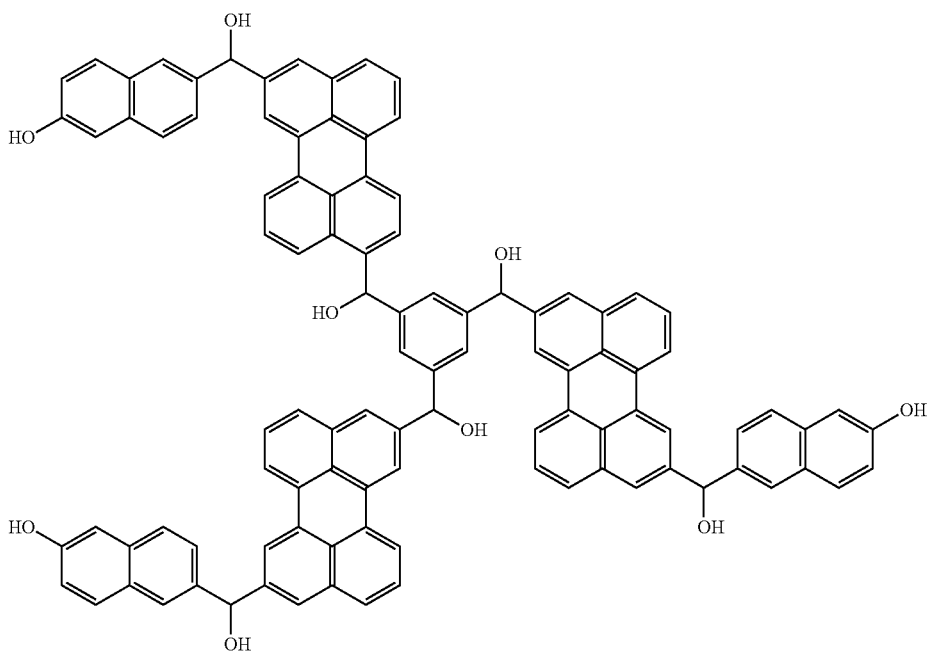

Comparative Synthesis Example 1

27.6 g (0.1 mol) of benzoperylene, 61 g (0.32 mol) of naphthoylchloride, and 500 g of mixed solution of chloroform/dichloromethane were put into a 2 L 3-necked flask and agitated by using a stirring magnetic bar, and 85.7 g (0.35 mol) of trichloroaluminum was little by little added thereto for a reaction. When the reaction was complete, the trichloroaluminum was removed by using water, obtaining a powdered reaction product. Subsequently, the reaction product was dissolved in tetrahydrofuran (THF), 18.98 g (0.5 mol) of lithium aluminumhydride was little by little added thereto for a reaction. When the reaction was complete, a mixture of water/methanol was used to remove by-products from the reaction, obtaining a monomer represented by the following Chemical Formula 15.

[Chemical Formula 15]

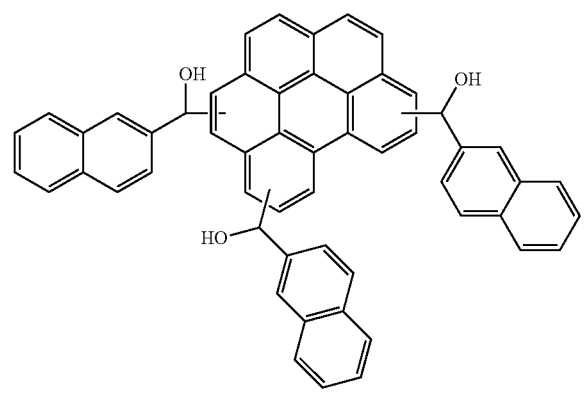

Comparative Synthesis Example 2

A 500 ml 3-necked flask equipped with a thermometer, a condenser, and a mechanical agitator was dipped in an oil thermostat at 90° C. to 100° C. A stirring magnetic bar was used for agitation, while a constant temperature was maintained. Subsequently, 28.83 g (0.2 mol) of 1-naphthol, 30.56 g (0.14 mol) of hydroxypyrene and 12.0 g (0.34 mol) of paraformaldehyde were put into the 3-necked flask, a solution prepared by dissolving 0.38 g (2 mmol) of p-toluene sulfonic acid monohydrate in 162 g of propylene glycol monomethyl ether acetate (PGMEA) was added to the 3-necked flask, and the resultant was agitated for 5 to 12 hours to perform a reaction.

When specimens were taken from the polymerization reactants by every hour to measure a weight average molecular weight, and the weight average molecular weight reached 1,800 to 2,000, the reaction was finished.

When the polymerization reaction was complete, the reactant was cooled down to room temperature and then, was added to 40 g of distilled water and 400 g of methanol, and the resultant was strongly agitated and then, allowed to stand. After removing a supernatant therefrom, a precipitate was dissolved in 80 g of propyleneglycol monomethyl ether acetate (PGMEA), 320 g of methanol was added thereto, the resultant was strongly agitated, and then allowed to stand (1st). Herein, a precipitate obtained after removing a supernatant obtained therefrom again was dissolved in 80 g of propyleneglycol monomethyl ether acetate (PGMEA) ($2^{nd}$). The 1st and $2^{nd}$ processes were called to be one purification process, and this purification process was three times in total performed. When the purification process was complete, an obtained polymer was dissolved in 80 g of propyleneglycol monomethyl ether acetate (PGMEA), methanol and distilled water remaining in the solution were removed under a reduced pressure, obtaining a polymer represented by the following Chemical Formula 16.

[Chemical Formula 16]

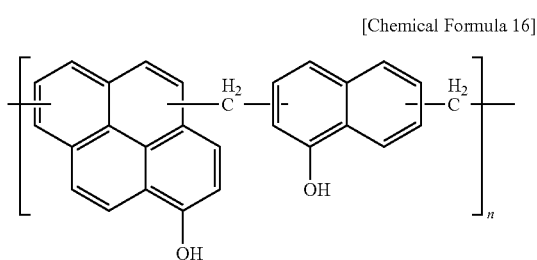

The polymer had a weight average molecular weight of 1,870 and polydispersity of 1.19.

Comparative Synthesis Example 3

First Step: Coupling Reaction 50.0 g (0.166 mol) of coronene, 46.8 g (0.333 mol) of benzoyl chloride, and 330 g of 1,2-dichloroethane were put into a flask. 44.4 g (0.333 mol) of aluminum chloride was slowly added to the solution, and the resultant was heated from room temperature to 60° C. and agitated for 8 hours. When the reaction was complete, a precipitate obtained by adding methanol to the solution was filtered and dried.

Second Step: Reduction Reaction 25.0 g (0.0492 mol) of the compound obtained in the first step and 174 g of tetrahydrofuran were put into a flask. 18.6 g (0.492 mol) of a sodium borohydride aqueous solution was slowly added to the solution, and the resultant was agitated at room temperature for 24 hours. When the reaction was complete, the reactant was neutralized into about pH 7 by using a 5% hydrogen chloride solution and then, extracted by using ethyl acetate, and an extract obtained therefrom was dried, obtaining a polymer represented by the following Chemical Formula 17.

[Chemical Formula 17]

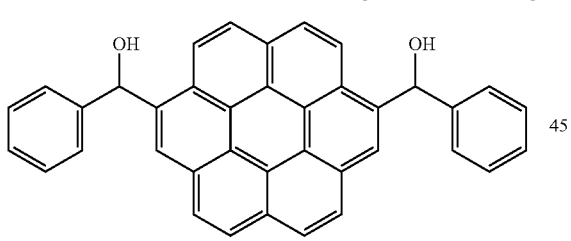

Comparative Synthesis Example 4

8.75 g (0.05 mol) of α, α'-dichloro-p-xylene, 26.66 g of aluminumchloride, and 200 g of γ-butyrolactone were put into a flask. Then, a solution prepared by dissolving 35.03 g (0.10 mol) of 4,4'-(9-fluorenylidene)diphenol in 200 g of γ-butyrolactone was slowly added to the solution, and the resultant was agitated at 120° C. for 12 hours. After the polymerization, an acid therein was removed by using water, and the remnant was concentrated. Subsequently, a polymerization product was diluted by using methylamyl ketone and methanol, and a solution prepared by mixing methylamyl ketone/methanol in a weight ratio of 4/1 was added thereto to adjust its concentration into 15 wt %. This solution was put into a separatory funnel, and n-heptane was added thereto to remove a monomer and a low molecular weight, obtaining a polymer represented by the following Chemical Formula 18.

[Chemical Formula 18]

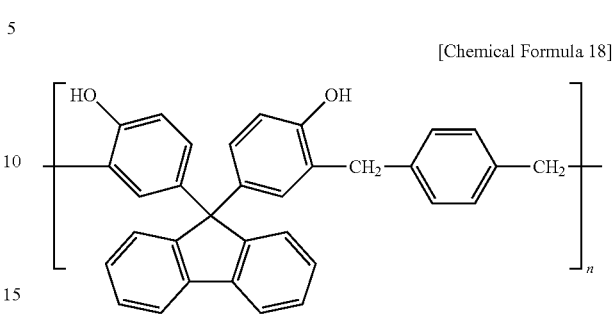

The polymer had a weight average molecular weight of 12,000 and polydispersity of 2.04.

Preparation of Hardmask Composition

Example 1

The compound obtained from Synthesis Example 1 was dissolved in a mixed solvent of propyleneglycol monomethyl ether acetate (PGMEA) and cyclohexanone in a ratio of 7:3 (v/v), and a precipitate produced therein was filtered, preparing a hardmask composition.

Examples 2 to 12

Each hardmask composition was prepared according to the same method as Example 1 except for respectively using the monomers of Synthesis Examples 2 to 12 instead of the monomer of Synthesis Example 1.

Comparative Examples 1 to 4

Each hardmask composition was prepared according to the same method as Example 1 except for respectively using the compounds according to Comparative Synthesis Examples 1 to 4 instead of the compound according to Synthesis Example 1.

Evaluation

Evaluation 1: Gap-Fill and Planarization Characteristics

Examples 1 to 4, and Comparative Examples 1 and 2

The hardmask compositions were respectively spin-on coated on each pattern wafer having a 1 μm-wide and 1.5 μm-deep hole and each pattern wafer having a 100 nm-wide and 1000 nm-deep hole and baked, and then, gap-fill and planarization characteristics of the hardmask compositions were examined by using a V-SEM equipment.

The gap-fill characteristics were evaluated by examining pattern cross-sections to have a void with a scanning electron microscope (SEM), and planarization characteristics were digitized according to the following Calculation Equation 1. As a difference between h1 and h2 is smaller, planarization characteristics are improved, and thus a smaller number represents excellent planarization characteristics.

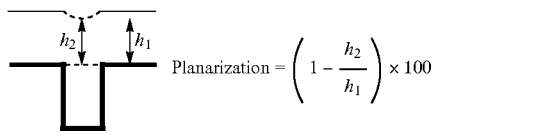

[Calculation Equation 1]

$$\text{Planarization} = \left(1 - \frac{h_2}{h_1}\right) \times 100$$

The result is provided in Table 1.

TABLE 1

| | Gap-fill characteristics (Void) | | Planarization characteristics (1500 rpm) |
|---|---|---|---|
| | Aspect ratio (1:1.5) | Aspect ratio (1:10) | |
| Example 1 | No void | No void | 20.23 |
| Example 2 | No void | No void | 25.34 |
| Example 3 | No void | No void | 22.17 |
| Example 4 | No void | No void | 19.89 |
| Comparative Example 1 | No void | No void | 28.31 |
| Comparative Example 2 | No void | Void | 39.55 |

Referring to Table 1, the hardmask compositions according to Examples 1 to 4 showed excellent planarization compared with the hardmask compositions according to Comparative Examples 1 and 2.

In addition, the hardmask compositions according to Examples 1 to 4 showed no void even at a relatively deep pattern (an aspect ratio=1: 10) and thus, showed excellent gap-fill characteristics. On the contrary, the hardmask compositions according to Comparative Example 2 had no void at a relatively low pattern (an aspect ratio=1: 1.5) but showed a void at a relatively deep pattern (an aspect ratio=1: 10).

Examples 5 to 9, and Comparative Example 3

The hardmask compositions including 13.0 wt % of a monomer according to Examples 5 to 9 and Comparative Example 3 were respectively spin-on coated on a pattern wafer and heat-treated at 400° C. for 2 minutes, and the surfaces of the cross-sections of the patterns were examined by using a V-SEM equipment.

The gap-fill characteristics were evaluated by examining the cross sections of a 40 nm-wide and 500 nm-deep pattern to check a void generation thereon, and the planarization characteristics were digitized according to the Calculation Equation 1 by examining the cross-sections of 180 nm-wide and 500 nm-deep patterns.

The results are provided in Table 2.

TABLE 2

| | Gap-fill characteristics | Planarization characteristics |
|---|---|---|
| Example 5 | No void | 6.5% |
| Example 6 | No void | 5.8% |
| Example 7 | No void | 7.8% |
| Example 8 | No void | 6.8% |
| Example 9 | No void | 7.5% |
| Comparative Example 3 | Void | 17.4% |

Referring to Table 2, the hardmask compositions according to Examples 5 to 9 had no void compared with the hardmask compositions according to Comparative Example 3 and thus, excellent gap-fill and planarization characteristics.

Examples 10 to 12

The hardmask compositions (a compound content: 10.0 wt %) according to Examples 10 to 12 were spin-on coated on a patterned silicon wafer and heat-treated at 400° C. for 120 seconds, and the gap-fill and planarization characteristics of the hardmask compositions were examined by using a field emission electron scanning microscope (FE-SEM) equipment.

The gap-fill characteristics were evaluated by examining the cross-section of a pattern to check if there was void therein by using a FE-SEM, and planarization characteristics were digitized according to Calculation Equation 1 by measuring the thickness of a hardmask layer based on the cross-section image of each pattern by using FE-SEM.

The results are provided in Table 3.

TABLE 3

| | Planarization characteristics | Gap-fill characteristics |
|---|---|---|
| Example 10 | 5.3% | No void |
| Example 11 | 9.3% | No void |
| Example 12 | 7.1% | No void |

Referring to Table 3, the thin films formed of the hardmask compositions according to Examples 10 to12 had excellent planarization and also, no void and thus, excellent gap-fill characteristic.

Evaluation 2: Heat Resistance

Examples 1 to 4, and Comparative Examples 1 and 2

The hardmask compositions according to Examples 1 to 4 and Comparative Examples 1 and 2 were respectively spin-on coated on a silicon wafer having silicon nitride and pre-baked to be about 800 Å-thick at 180° C. for 60 second, and then, out-gas generated during baking at 400° C. for 120 seconds were measured by using QCM (Quartz Crystal Microbalace)

The out-gas evaluation results are provided in Table 4.

TABLE 4

| | Amount of out-gas (ng) |
|---|---|
| Example 1 | 43 |
| Example 2 | 52 |
| Example 3 | 38 |
| Example 4 | 60 |
| Comparative Example 1 | 175 |
| Comparative Example 2 | 77 |

Referring to Table 4, the hardmask compositions according to Examples 1 to 4 generated out-gas of less than or equal to 60 ng while baked at a high temperature of 400° C. and turned out to be stably processed at a high temperature. On the contrary, the hardmask compositions according to Comparative Examples 1 and 2 generated relatively more out-gas and turned out to be inappropriate for a high temperature process.

Examples 5 to 9, and Comparative Example 3

The hardmask compositions including 5.0 wt % of a monomer according to Examples 5 to 9 and Comparative Example 3 were respectively spin-on coated on a silicon wafer and heat-treated on a hot plate at 240° C. for one minute, forming thin films. The thicknesses of the initial thin films were measured by using a thickness measuring device made by K-MAC. Then, the thin films were heat-treated again at 400° C. for 2 minute, the thicknesses of the thin films were measured, and then, thickness decrease ratios of the thin films were calculated according to the following Calculation Equation 2.

Thickness decrease ratio of thin film=(thickness of thin film after baked at 240° C.–thickness of thin film after baked at 400° C.)/thickness of thin film after baked at 240° C.×100(%) [Calculation Equation 2]

On the other hand, the hardmask compositions according to Examples 5 to 9 and Comparative Example 3 were spin-on coated on a silicon wafer and pre-baked at 180° C. for 60 seconds, and out-gas generated during baked at 400° C. for 120 seconds was measured by using QCM (Quartz Crystal Microbalace).

The thickness decrease ratio of thin film and out-gas results are provided in Table 5.

TABLE 5

| | Thickness decrease ratio of thin film (%) | Amount of out-gas (ng) |
|---|---|---|
| Example 5 | −5.75 | 24 |
| Example 6 | −5.87 | 20 |
| Example 7 | −8.82 | 25 |
| Example 8 | −9.98 | 37 |
| Example 9 | −10.32 | 52 |
| Comparative Example 3 | −34.08 | 180 |

Referring to Table 5, the thin films formed of the hardmask compositions according to Examples 5 to 9 had a less thickness decrease ratio than the film formed of the hardmask composition according to Comparative Example 3 during the heat treatment at 400° C.

In addition, the hardmask compositions according to Examples 5 to 9 generated relatively less out-gas than the hardmask composition during the heat treatment at 400° C. high temperature 400° C. and thus, turned out stable for a high temperature process. On the contrary, the hardmask composition according to Comparative Example 3 generated more out-gases and turned out in appropriate for a high temperature process.

In addition, the hardmask compositions according to Examples 5 to 9 formed a more highly cross-linked thin film than the hardmask composition according to Comparative Example 3 400° C. and thus, had high heat resistance at a high temperature.

Examples 10 to 12

The heat resistance of the hardmask compositions according to Examples 10 to 12 was evaluated according to the same methods as Examples 5 to 9 except for changing the amount of a monomer into 10 wt %.

The results are provided in Table 6.

TABLE 6

| | Thickness decrease ratio of thin film (%) | Amount of out-gas (ng) |
|---|---|---|
| Example 10 | −4.39 | 21 |
| Example 11 | −3.96 | 32 |
| Example 12 | −4.31 | 24 |

Referring to Table 6, the hardmask compositions according to Examples 10 to 12 turned out to form a thin film having a low thickness decrease ratio at a high temperature and small out-gas and thus, had high heat resistance.

Evaluation 3: Etch Resistance

The hardmask compositions (a compound content: 13 wt %) according to Examples 5 to 12 and Comparative Example 4 were spin-on coated on a silicon wafer and heat-treated on a hot plate at 400° C. for 2 minutes, forming thin films. Then, thicknesses of the thin films were measured. The thin films were dry-etched by respectively using a mixed gas of $N_2/O_2$ and $CF_x$ gas for 60 seconds and 100 seconds, and then, thicknesses of the thin films were measured again. The thicknesses of the thin films before and after the dry etching and etching time were used to calculate a bulk etch rate (BER) according to the following Calculation Equation 3.

(Initial thin film thickness–thin film thickness after etching)/etching time(Å/s) [Calculation Equation 3]

The results are provided in Table 7.

TABLE 7

| | Etch rate ($N_2/O_2$, Å/s) | Etch rate ($CF_x$) |
|---|---|---|
| Example 5 | 22.5 | 26.1 |
| Example 6 | 22.3 | 25.7 |
| Example 7 | 22.5 | 26.7 |
| Example 8 | 23.9 | 28.8 |
| Example 9 | 24.2 | 26.5 |
| Example 10 | 20.4 | 25.1 |
| Example 11 | 19.8 | 24.1 |
| Example 12 | 20.9 | 24.8 |
| Comparative Example 4 | 26.7 | 32.0 |

Referring to Table 7, thin films formed of the hardmask compositions according to Examples 5 to 12 had sufficient etching resistance for etching gas compared with a thin film formed of the hardmask composition according to Comparative Example 4 and thus, a low etch rate.

Evaluation 4: Pattern Formation

A 3000 Å-thick silicon oxide ($SiO_2$) layer was formed on a silicon wafer in a chemical vapor deposition method. Subsequently, the hardmask compositions (a compound content: 15 wt %) according to Examples 5 to 12 and Comparative Examples 3 and 4 were respectively spin-on coated on the silicon oxide layer and heat-treated on a hot plate at 400° C. for 2 minutes to form hardmask layers. On the hardmask layers, silicon nitride (SiN) layers were formed using a chemical vapor deposition method. On the silicon nitride layers, photoresists for KrF were coated, heat-treated at 110° C. for 60 seconds, exposed to light by using an ASML (XT: 1400, NA 0.93) exposure equipment, and developed in a 2.38 wt % tetramethylammonium hydroxide (TMAH) aqueous solution. The patterned photoresists were used as a mask to dry-etch the silicon nitride layers by using a mixed gas of $CHF_3/CF_4$. The patterned silicon nitride layers were used as a mask to dry-etch the hardmask layers by using a mixed gas of $N_2/O_2$, and the patterned hardmask layers were used as a mask to dry-etch the silicon oxide layers by using a mixed gas of $CHF_3/CF_4$. Then, $O_2$ gas was used to remove an organic material remaining therein.

Pattern cross-sections of the hardmask layers and the silicon oxide layers were examined by using an electron scanning microscope (SEM).

The results are provided in Table 8.

TABLE 8

| | Hardmask layer pattern profile | Silicon oxide layer pattern profile |
|---|---|---|
| Example 5 | vertical shape | vertical shape |
| Example 6 | vertical shape | vertical shape |
| Example 7 | vertical shape | vertical shape |
| Example 8 | vertical shape | vertical shape |
| Example 9 | vertical shape | vertical shape |
| Example 10 | vertical shape | vertical shape |
| Example 11 | vertical shape | vertical shape |
| Example 12 | vertical shape | vertical shape |
| Comparative Example 3 | tapered shape | tapered shape |
| Comparative Example 4 | tapered shape | tapered shape |

Referring to Table 8, the hardmask layers formed of the hardmask compositions according to Examples 5 to 12 and the silicon oxide layers therebeneath were all patterned in a vertical shape, while the hardmask layers formed of the hardmask compositions according to Comparative Examples 3 and 4 were patterned in a tapered shape. Accordingly, the hardmask compositions according to Examples 5 to 12 had excellent etching resistance compared with the hardmask compositions according to Comparative Examples 3 and 4 and formed a satisfactory pattern, and thus, the material layers therebeneath was satisfactorily patterned.

Evaluation 5: Optical Properties

The hardmask compositions according to Examples 1 to 4 and Comparative Examples 1 and 2 were spin-on coated on a silicon wafer on which silicon nitride was formed and baked at 400° C. for 120 seconds, forming about 800 Å-thick hardmask layers.

Refractive indices (n) and extinction coefficients (k) of the hardmask layers were measured. The refractive indices and extinction coefficients were measured by radiating a ray having a wavelength ranging from 193 nm to 633 nm by using Ellipsometer (J.A.Woollam Co., Inc.).

The results are provided in Table 9.

TABLE 9

| | Optical properties (193 nm) | | Optical properties (633 nm) | |
|---|---|---|---|---|
| | refractive index(n) | extinction coefficient(k) | refractive index(n) | extinction coefficient(k) |
| Example 1 | 1.453 | 0.593 | 1.868 | 0.046 |
| Example 2 | 1.430 | 0.539 | 1.857 | 0.055 |
| Example 3 | 1.448 | 0.560 | 1.862 | 0.058 |
| Example 4 | 1.408 | 0.532 | 1.888 | 0.075 |
| Comparative Example 1 | 1.295 | 0.525 | 1.946 | 0.108 |
| Comparative Example 2 | 1.410 | 0.523 | 1.955 | 0.217 |

Referring to Table 9, hardmask layers formed of the hardmask compositions according to Examples 1 to 4 had a refractive index (n) and an extinction coefficient (k) appropriately used as a hardmask layer even in a patterning process using a light source having a low wavelength of 193 nm.

In addition, since the hardmask layers formed of the hardmask compositions according to Examples 1 to 4 had a low extinction coefficient (k) of less than or equal to 0.1 at 633 nm, the hardmask compositions turned out to form a 10,000 Å-50,000 Å-thick hardmask layer. On the contrary, since the hardmask layers formed of the hardmask compositions according to Comparative Examples 1 and 2 had a high extinction coefficient (k) of greater than 0.1 at 633 nm, the hardmask compositions turned out inappropriate for a process requiring a thick hardmask such as a metal pattern.

Evaluation 6: Thickness Evaluation with Maximum Solid Content

Maximum solubility of the hardmask compositions according to Examples 1 to 4 and Comparative Example 1 in a PGMEA (Propylene Glycol Methyl Ether Acetate) solvent at room temperature was confirmed. The hardmask compositions were respectively coated on a silicon wafer on which silicon nitride was formed and baked at 240° C. for one minute, and then, thicknesses of the hardmask layers formable with a maximum solid content were measured.

The results are provided in Table 10.

TABLE 10

| | Maximum solid content (wt %, in PGMEA) | Film thickness (μm) |
|---|---|---|
| Example 1 | 30 | 1.8 |
| Example 2 | 27 | 1.9 |
| Example 3 | 37 | 2.6 |
| Example 4 | 30 | 2.1 |
| Comparative Example 1 | 17 | 0.75 |

Referring to Table 10, the hardmask compositions according to Examples 1 to 4 had high solubility, thereby maximum solid contents increased, and thus thick films were formed. On the contrary, the hardmask composition according to Comparative Example 1 had relatively low solubility, thereby a maximum solid content decreases, and thus, a thin film was formed.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A monomer for a hardmask composition, the monomer being represented by the following Chemical Formula 1:

[Chemical Formula 1]

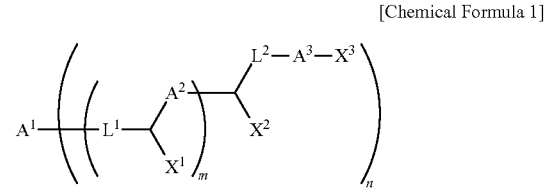

wherein, in the above Chemical Formula 1, $A^1$ to $A^3$ are each independently a substituted or unsubstituted aliphatic or aromatic cyclic group, wherein at least one of $A^1$ to $A^3$ is a polycyclic aromatic group;

$X^1$ to $X^3$ are each independently hydrogen, a hydroxy group, a substituted or unsubstituted amino group, a halogen atom, a halogen-containing group, or a combination thereof, $L^1$ and $L^2$ are each independently a single bond or a substituted or unsubstituted C1 to C6 alkylene group, n is an integer ranging from 2 to 5, and m is an integer ranging from 1 to 3.

2. The monomer as claimed in claim 1, wherein $A^1$ to $A^3$ are each independently a substituted or unsubstituted aliphatic or aromatic cyclic group selected from the following Group 1:

[Group 1]

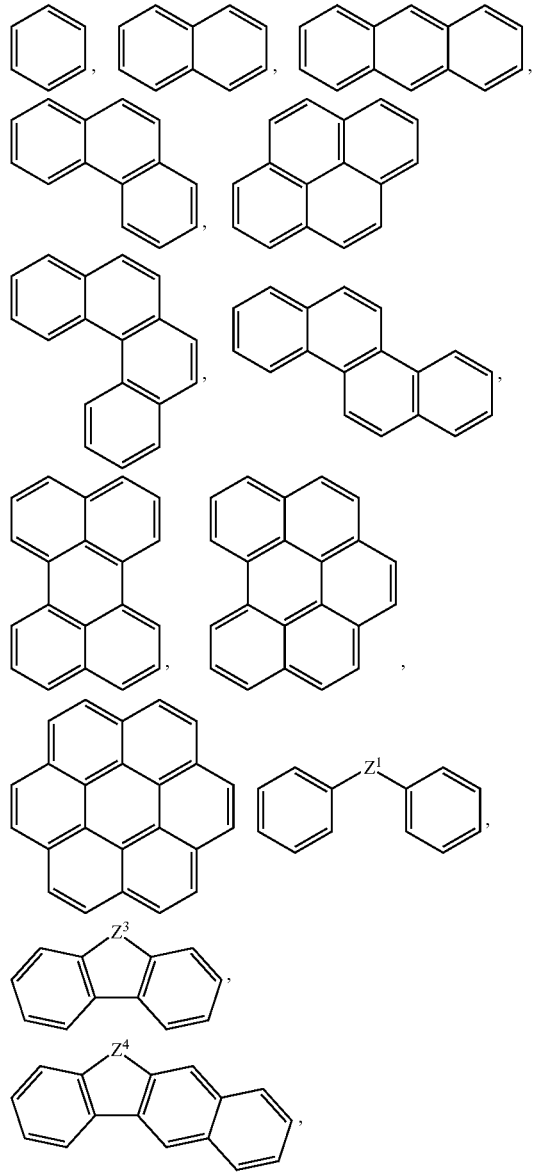

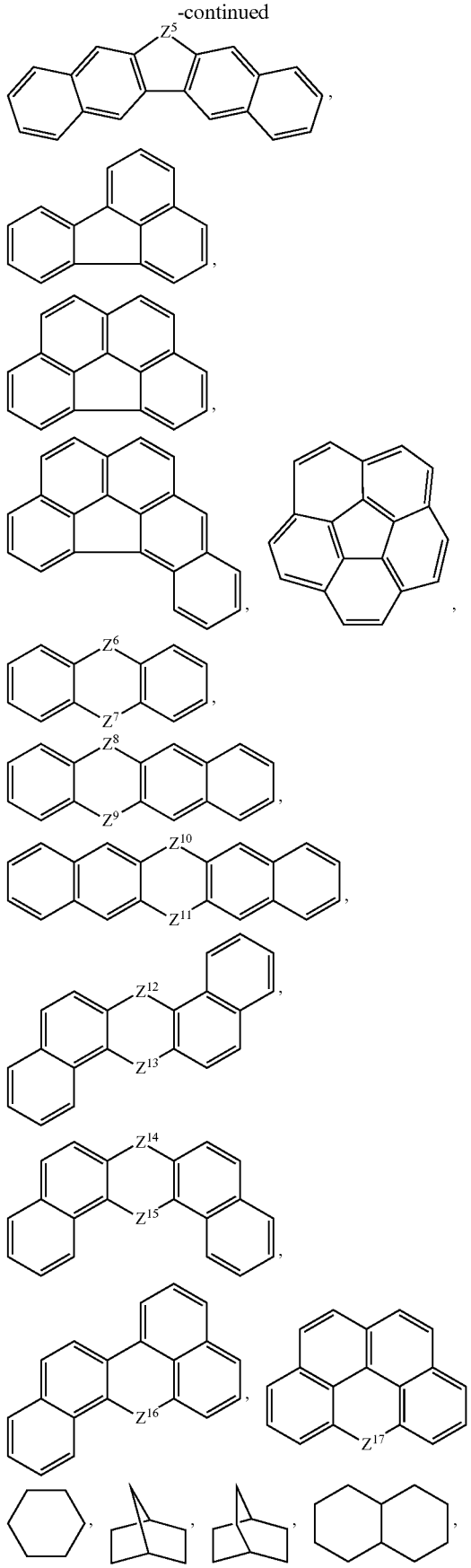

-continued

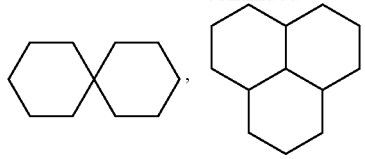

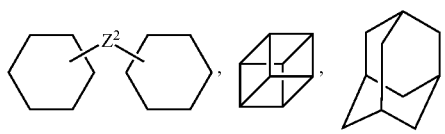

wherein, in the Group 1,

Z$^1$ and Z$^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein R$^a$ is hydrogen, a substituted or unsubstituted C1 to C 10 alkyl group, a halogen atom, or a combination thereof, and Z$^3$ to Z$^{17}$ are independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a halogen atom, a halogen-containing group, or a combination thereof.

3. The monomer as claimed in claim 1, wherein A$^1$ and A$^3$ are each independently a benzene group, a naphthalene group, a biphenyl group, or a pyrene group, and A$^2$ is a pyrene group, a perylene group, a benzoperylene group, or a coronene group.

4. The monomer as claimed in claim 1, the monomer being represented by the following Chemical Formula 2 or 3:

[Chemical Formula 2]

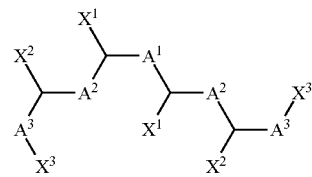

[Chemical Formula 3]

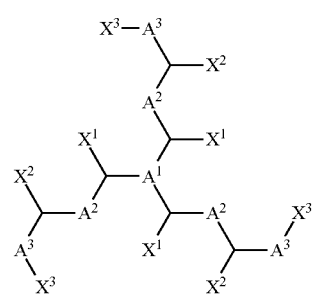

wherein, in the above Chemical Formula 2 and 3,

A$^1$ to A$^3$ and X$^1$ to X$^3$ are each independently defined the same as those of Chemical Formula 1.

5. The monomer as claimed in claim 4, the monomer being represented by one selected from the following Chemical Formulae 4 to 14:

[Chemical Formula 4]

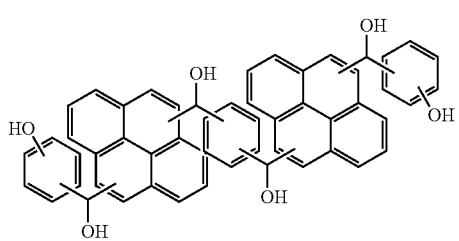

[Chemical Formula 5]

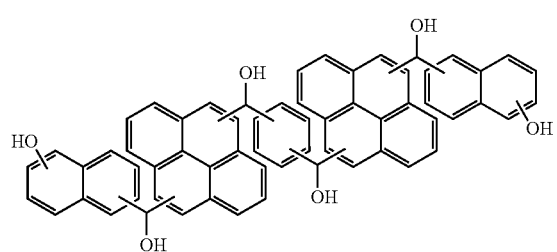

[Chemical Formula 6]

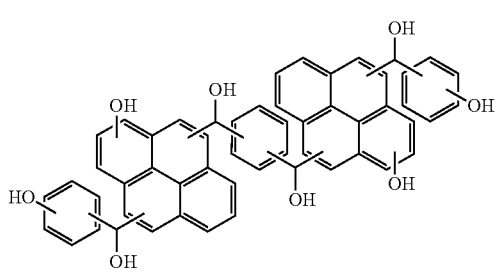

[Chemical Formula 7]

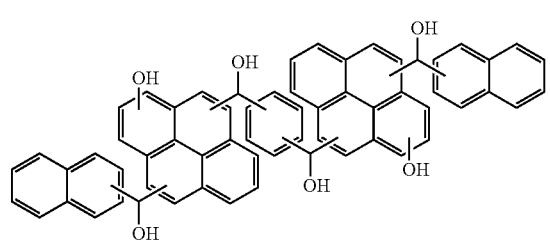

[Chemical Formula 8]
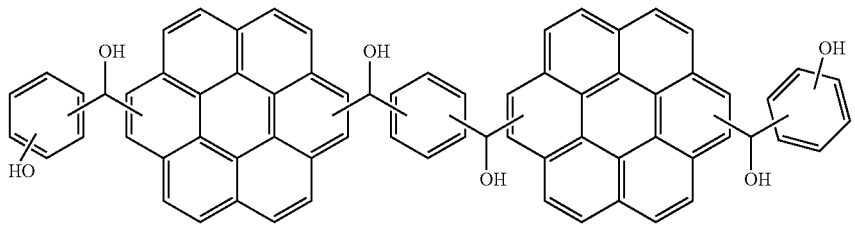
[Chemical Formula 9]
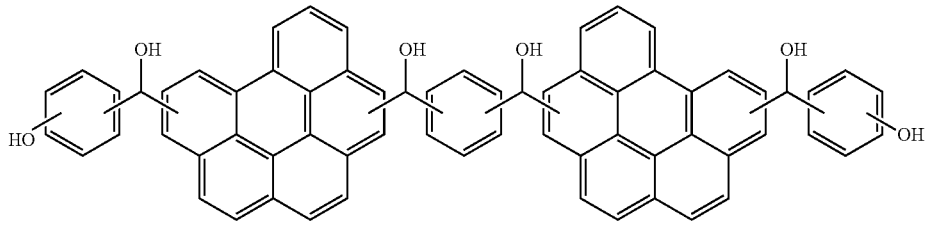
[Chemical Formula 10]
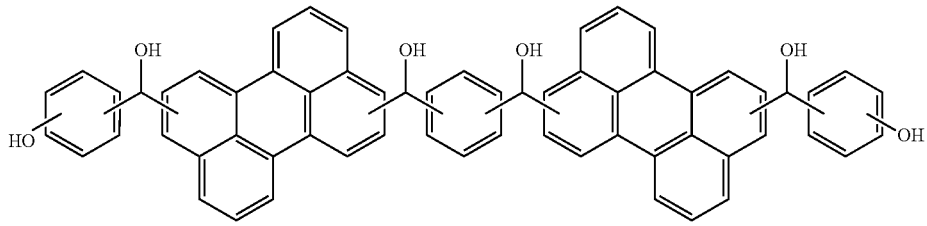
[Chemical Formula 11]
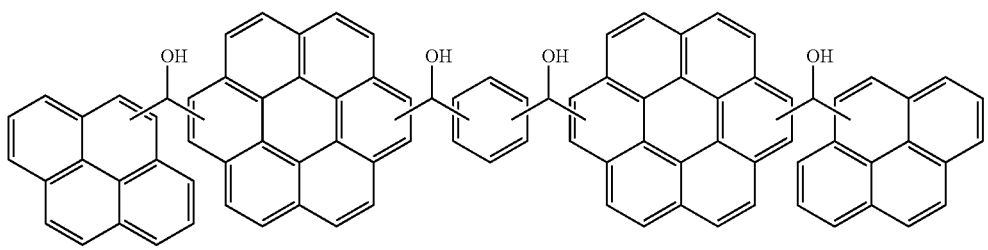
[Chemical Formula 12]
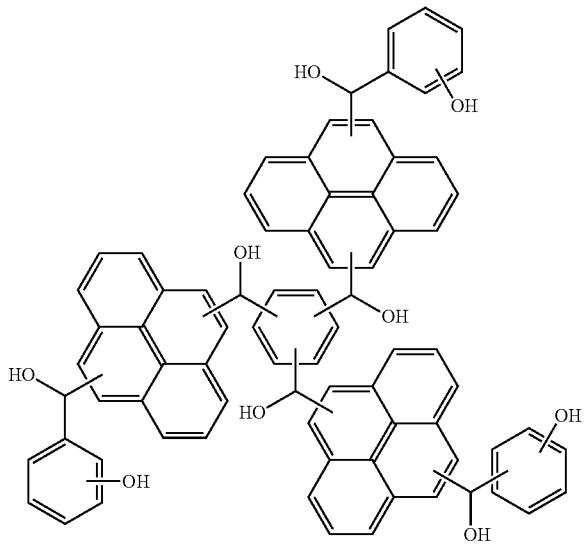

-continued

[Chemical Formula 13]

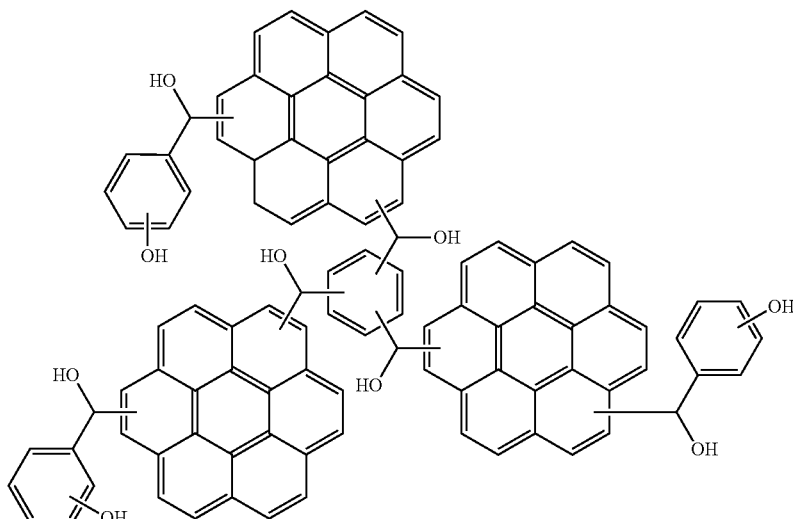

[Chemical Formula 14]

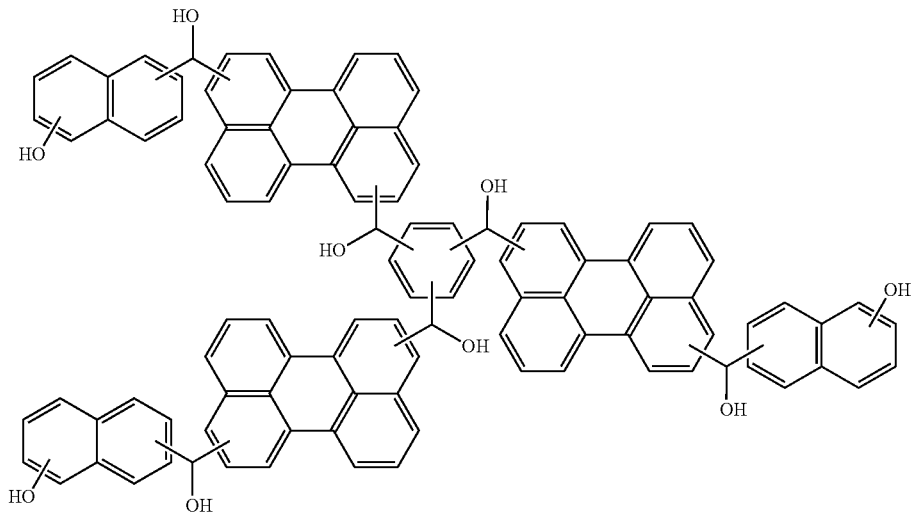

6. The monomer as claimed in claim 1, wherein the monomer has a molecular weight of 500 to 5,000.

7. A hardmask composition, comprising
a monomer represented by the following Chemical Formula 1, and
a solvent:

[Chemical Formula 1]

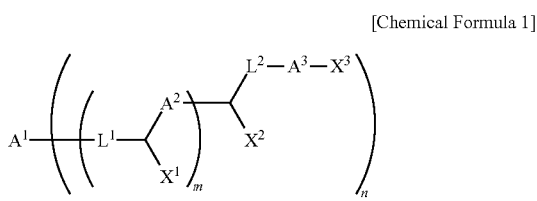

wherein, in the above Chemical Formula 1,
$A^1$ to $A^3$ are each independently a substituted or unsubstituted cyclic group, wherein at least one of the $A^1$ to $A^3$ is a polycyclic aromatic group,
$X^1$ to $X^3$ are each independently hydrogen, a hydroxy group, a substituted or unsubstituted amino group, a halogen atom, a halogen-containing group, or a combination thereof,
$L^1$ and $L^2$ are each independently a single bond or a substituted or unsubstituted C1 to C6 alkylene group,
n is an integer ranging from 2 to 5, and
m is an integer ranging from 1 to 3.

8. The hardmask composition as claimed in claim 7, wherein $A^1$ to $A^3$ are each independently a substituted or unsubstituted aliphatic or aromatic cyclic group selected from the following Group 1:

[Group 1]

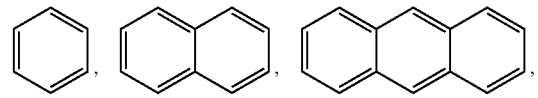

-continued
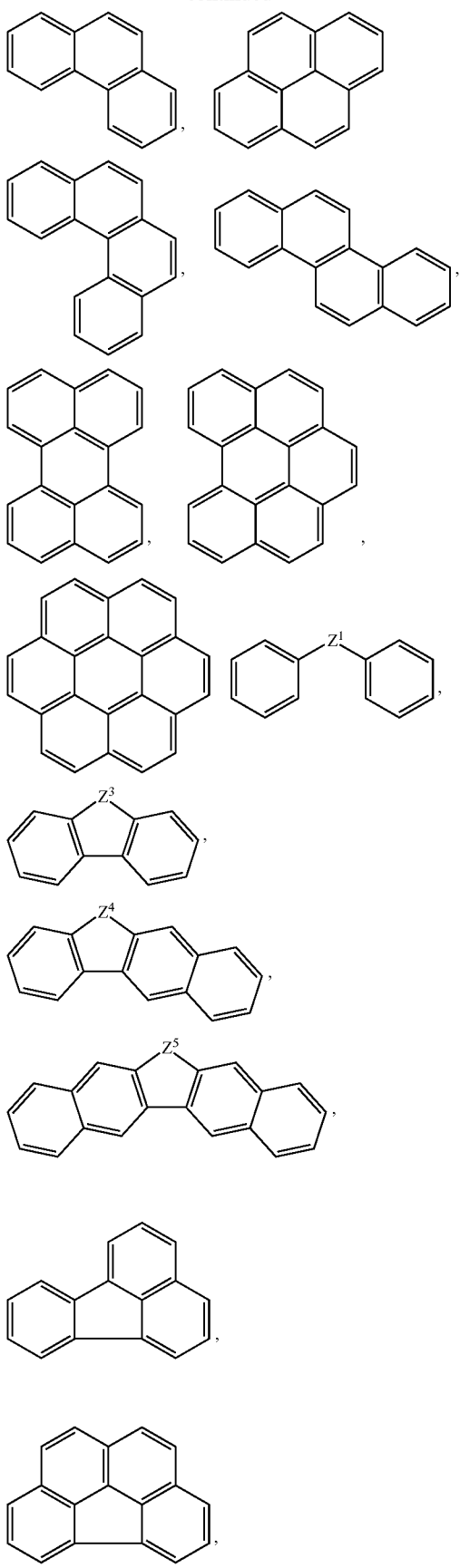
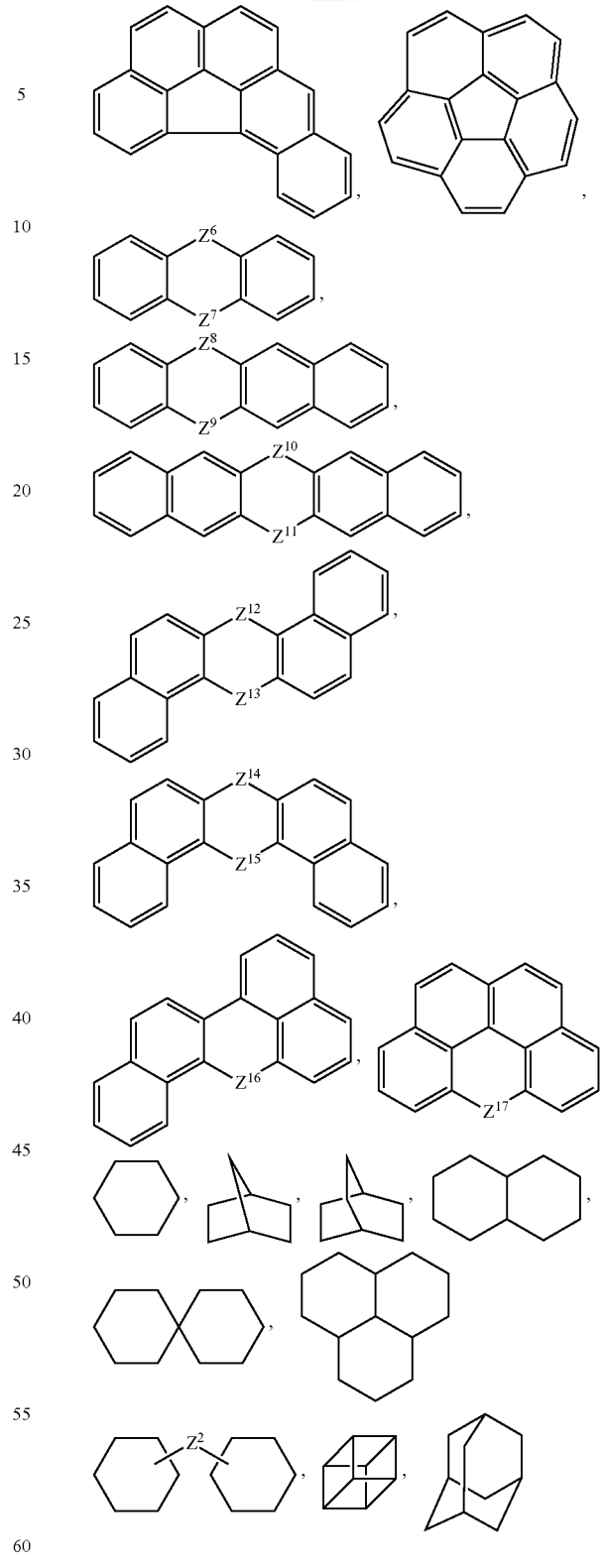
wherein, in the Group 1,
Z¹ and Z² are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein le is hydrogen, a substituted or unsubstituted C1 to C10 alkyl group, a halogen atom, or a combination thereof, and $Z^3$ to $Z^{17}$ are independently C=O, NR$^a$, oxygen (O), sulfur (S), CR$^b$R$^{c'}$ or a combination thereof, wherein R$^a$ to R$^c$ are each independently hydrogen, a substituted or unsubstituted C1 to C10 alkyl group, a halogen atom, a halogen-containing group, or a combination thereof.

9. The hardmask composition as claimed in claim 7, wherein $A^1$ and $A^3$ are each independently a benzene group, a naphthalene group, biphenyl group or a pyrene group, and $A^2$ is a pyrene group, a perylene group, a benzoperylene group, or a coronene group.

10. The hardmask composition as claimed in claim 7, wherein the monomer is represented by the following Chemical Formula 2 or 3:

[Chemical Formula 2]

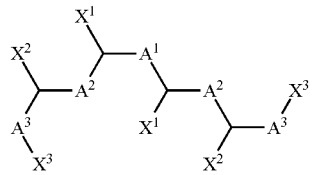

[Chemical Formula 3]

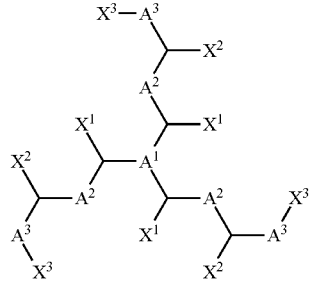

wherein, in the above Chemical Formula 2 and 3,
$A^1$ to $A^3$ and $X^1$ to $X^3$ are each independently defined the same as those in Chemical Formula 1.

11. The hardmask composition as claimed in claim 10, wherein the monomer is represented by one selected from the following Chemical Formulae 4 to 14:

[Chemical Formula 4]

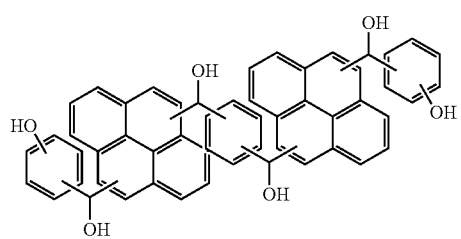

[Chemical Formula 5]

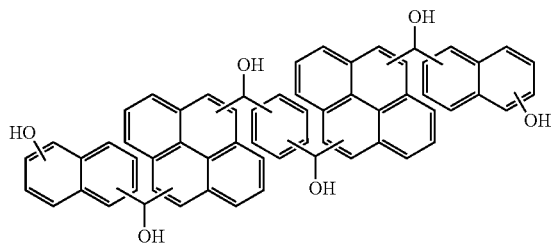

[Chemical Formula 6]

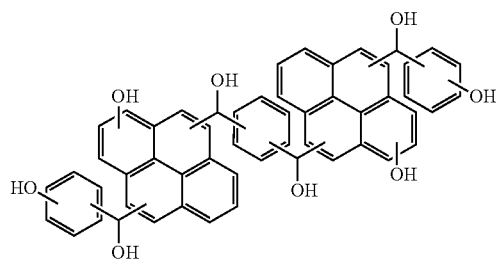

[Chemical Formula 7]

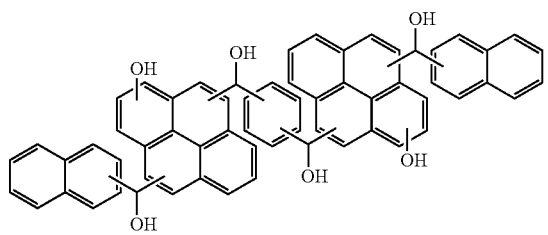

[Chemical Formula 8]

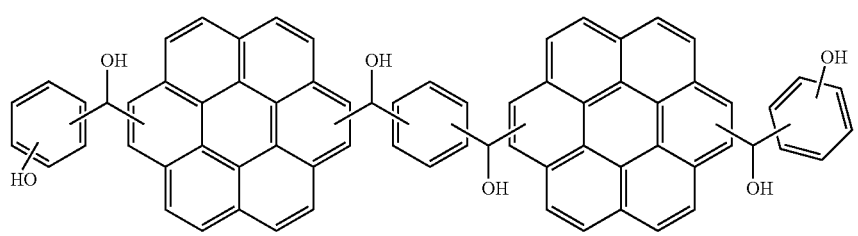

[Chemical Formula 9]
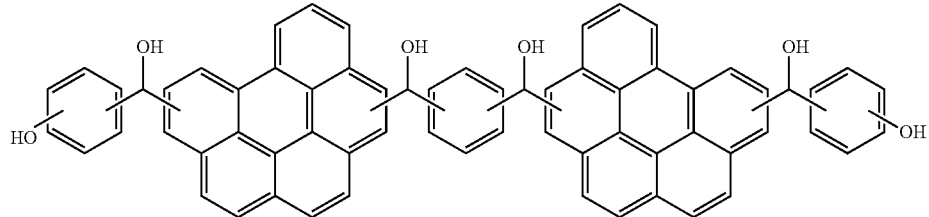
[Chemical Formula 10]
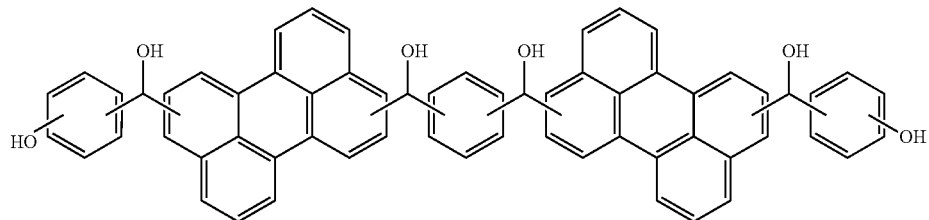
[Chemical Formula 11]
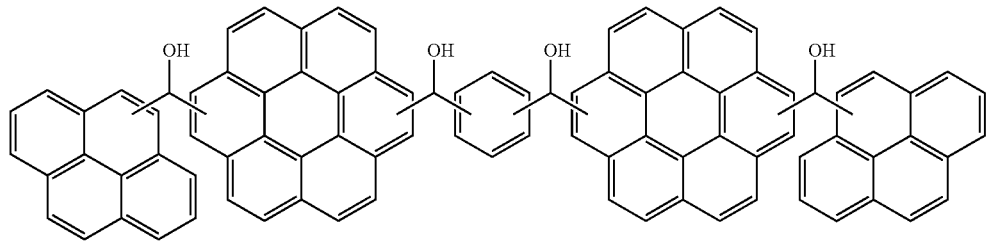
[Chemical Formula 12]
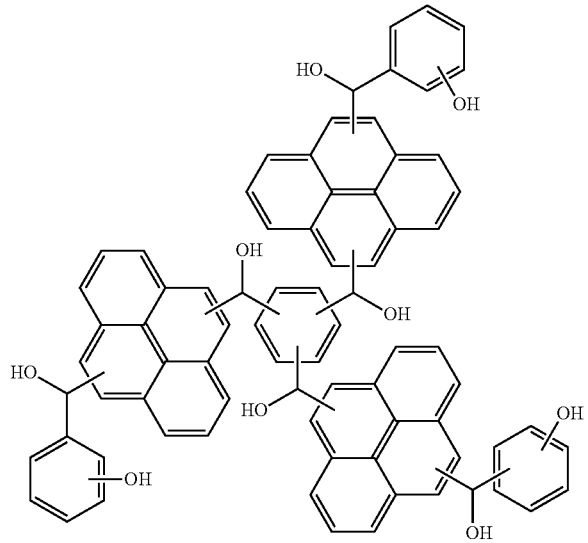

[Chemical Formula 13]

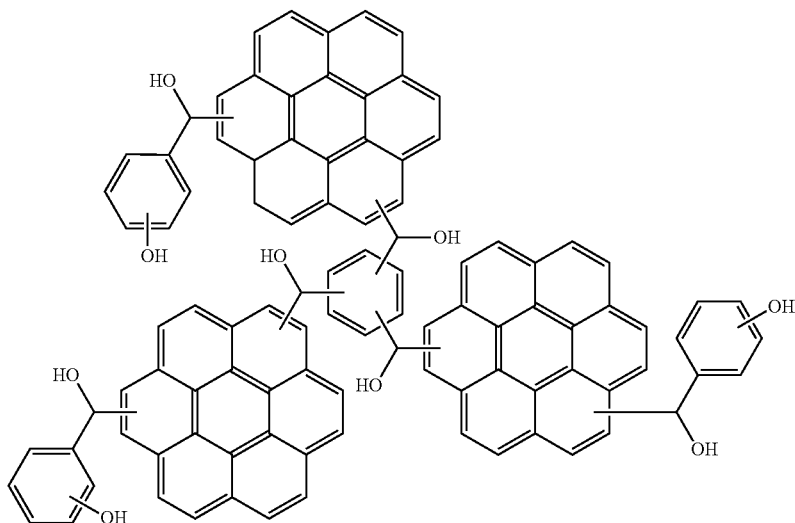

[Chemical Formula 14]

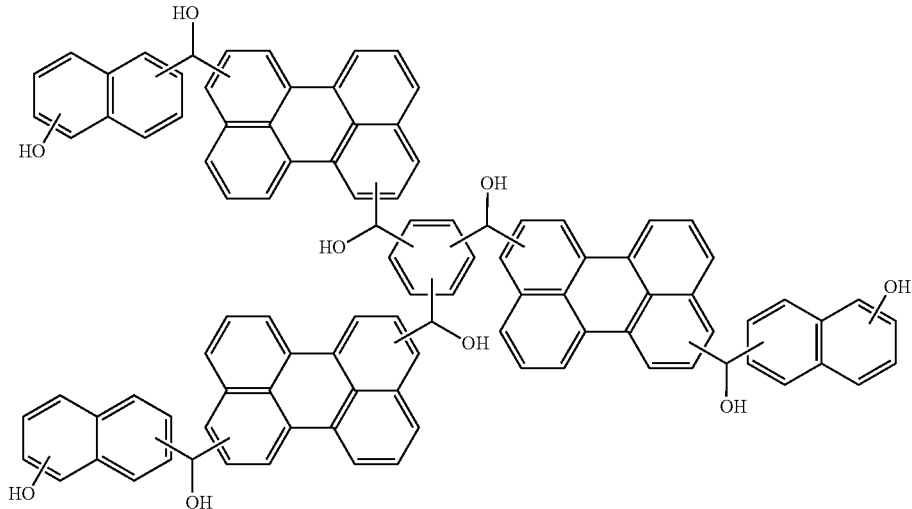

12. The hardmask composition as claimed in claim 7, wherein the monomer has a molecular weight of 500 to 5,000.

13. The hardmask composition as claimed in claim 7, wherein the monomer is included in an amount of 0.1 to 50 wt% based on the total amount of the hardmask composition.

14. A method of forming patterns, comprising
providing a material layer on a substrate,
applying the hardmask composition as claimed in claim 7 on the material layer,
heat-treating the hardmask composition to form a hardmask layer,
forming a silicon-containing thin layer on the hardmask layer,
forming a photoresist layer on the silicon-containing thin layer,
exposing and developing the photoresist layer to form a photoresist pattern
selectively removing the silicon-containing thin layer and the hardmask layer using the photoresist pattern to expose a part of the material layer, and
etching an exposed part of the material layer.

15. The method as claimed in claim 14, wherein the hardmask composition is applied using a spin-on coating method.

* * * * *